(12) United States Patent  
Matoba

(10) Patent No.: US 6,899,538 B2  
(45) Date of Patent: May 31, 2005

(54) IDENTIFICATION TYPE INSTRUMENT ASSEMBLY, IDENTIFICATION TYPE ADAPTER, IDENTIFICATION TYPE TUBE, AND MEDICAL APPARATUS USING THEM

(75) Inventor: Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 140 days.

(21) Appl. No.: 09/909,026

(22) Filed: Jul. 19, 2001

(65) Prior Publication Data

US 2003/0165794 A1 Sep. 4, 2003

(51) Int. Cl.$^7$ ................................................. A61C 3/00
(52) U.S. Cl. ...................................................... 433/114
(58) Field of Search ................................... 433/77, 114

(56) References Cited

U.S. PATENT DOCUMENTS

| | | | |
|---|---|---|---|
| 4,705,038 A | * | 11/1987 | Sjostrom et al. |
| 5,162,725 A | * | 11/1992 | Hodson et al. |
| 5,383,874 A | * | 1/1995 | Jackson et al. ................. 601/1 |
| 5,400,267 A | * | 3/1995 | Denen et al. |
| 5,609,560 A | * | 3/1997 | Ichikawa et al. ........... 600/101 |
| 6,017,354 A | * | 1/2000 | Culp et al. ................... 606/170 |
| 6,019,775 A | * | 2/2000 | Sakurai ....................... 606/169 |

\* cited by examiner

Primary Examiner—Ralph A. Lewis
(74) Attorney, Agent, or Firm—Koda & Androlia

(57) ABSTRACT

An identification type instrument assembly detachably connected to a main body of a medical apparatus for use in diagnosis and treatment. The instrument assembly is provided with identification signal output means for actively outputting unique self-identification signals prepared in advance under a predetermined procedure, and the connected instrument assembly can be specified in the main body by the identification signals outputted from the identification signal output means when the instrument assembly is connected to the main body.

17 Claims, 20 Drawing Sheets

(a)
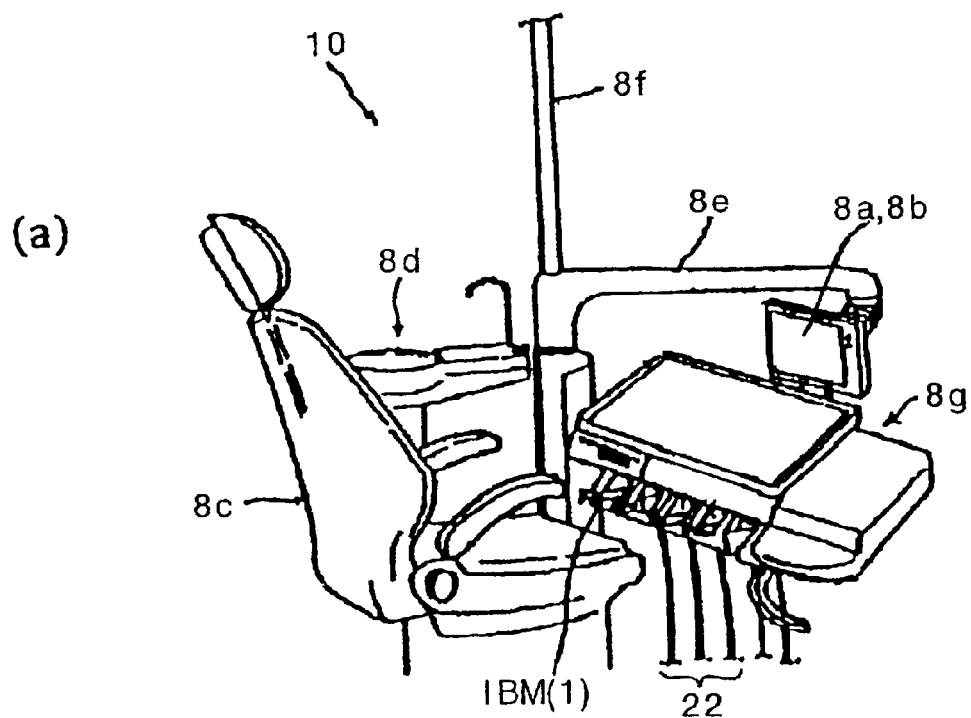
(b)
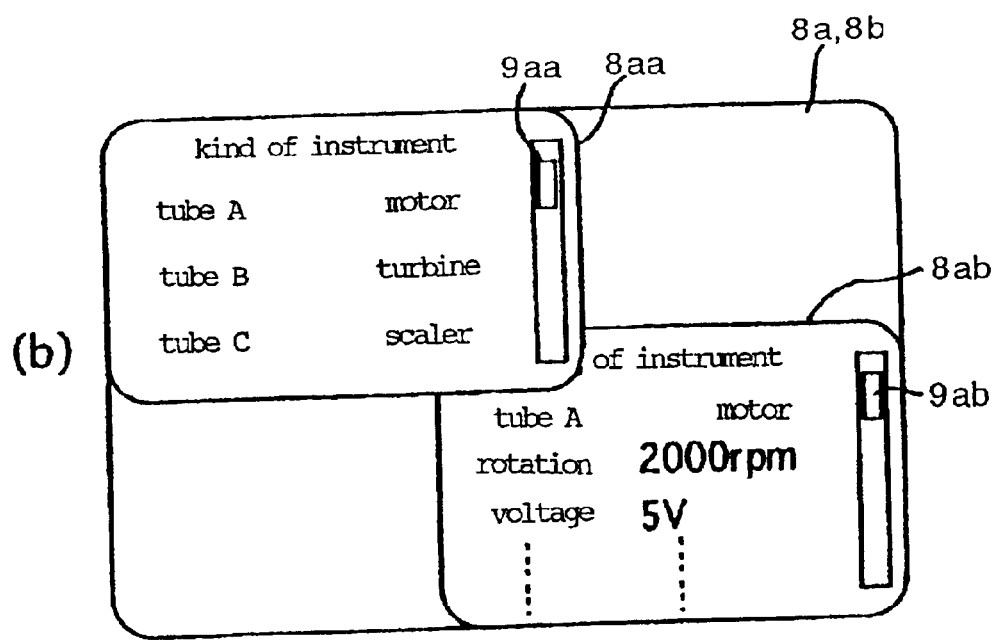
Fig.12

IDENTIFICATION TYPE INSTRUMENT ASSEMBLY, IDENTIFICATION TYPE ADAPTER, IDENTIFICATION TYPE TUBE, AND MEDICAL APPARATUS USING THEM

BACKGROUND OF THE INVENTION

1. Field of the Invention

The present invention relates to an identification type instrument assembly detachably connected to the main body of a medical apparatus for use in diagnosis and treatment, an: identification type adapter and an identification type tube connecting an instrument and the main body.

2. Prior Art

In medical or dental care, there is a medical apparatus in which medical treatment is executed by instruments connected to its main body and for supplying electric, power, water and air, or by controlling plural instruments with independent driving sources. Such an instrument includes a medical cutting apparatus such as a motor handpiece, a turbine handpiece, a scaler, an apparatus using ultrasonic wave or light such as a photo polymerization apparatus, a measurement and observation apparatus such as a measuring device of root canal length and an intraoral camera in dental field.

Conventionally according to the dental apparatus, each such instruments have been connected to the main body via an exclusive tube and a driving circuit, a water circuit, and an air circuit required for the connected instrument and which are provided in the main body.

Whereas in such a method, as the kinds of instruments used in the medical apparatus are increased, the number of connections provided for the apparatus and the number of exclusive tubes in the main body are increased. On the other hand, the number of connections can't be increased immoderately because of restriction of the entire apparatus and it hasn't been preferable to increase the number of tubes because of space problems and entwining of each of the tubes.

However, as kinds of new instruments have been increased according to the development of new medical technology, it has become a big problem to be solved how to deal with the increase in the kinds of the instruments and several solutions have been proposed.

For example, an instrument shown in FIG. 17 has been proposed in JP-B-8-115.

Instruments 101a–101d are used by detachably being fitted to a common tube 102 through ends 103a–103c inserted detachably or directly. Connections between the ends 103a–103c and the instrument 101d, and the tube 102 are constructed as multi connection 104 so that plural instruments 101a–101d can be detachably exchanged and used for one common tube 102.

Required connection terminals are provided for connection parts 104a–104d of the ends 103a–103c and the instrument 101d. The connection terminals are located according to a predetermined arrangement, and any connection parts 104a–104d are connected to the connection part 104e of the tube so that air, water, and electric power required for each instrument 101a–101d can be received via the tube 102 from the main body (not shown).

According to such construction, plural kinds of instruments 101a–101d can be detachably exchanged and used for one tube 102 and the problem of the increase of the number of the tubes 102 has been solved.

On the other hand in this method, the main body requires identification of which instrument is fitted to the tube 102 to supply electric power suitable for the fitted instrument to drive the instrument. For this purpose, in this embodiment, resistances 105a–105f having different resistance values are housed in the instruments 101a–101d or in the ends 103b, 103c, and when the instrument is fitted, electric power is supplied form the main body and the fitted instrument is specified by measuring the resistance values of the resistance 105a–105f.

The instrument shown in FIG. 18 is proposed in JP-B-3-34345. FIG. 18(a) shows an outer view of its using condition and FIG. 18(b) shows a detailed view of its connection part.

The instruments 201a–201c are provided with exclusive tubes 202a–202c respectively and these tubes 202a–202c are fitted to the main body 210a detachably and exchangeably. The connection of the tubes 202a–202c and the main body is constructed as a multi joint connection 204.

The multi joint connection 204 is the same as the multi joint type of the connection parts 104a–104d in FIG. 17. The same connection part 204d of multi joint type is provided at four places of the main body 210a and any tubes 202a–202c can be connected to each connection part 204d and can be used by operating a foot controller 210b provided for the main body 210a.

Also according to such construction, instruments more than the number of the connection parts 204d can be detachably and exchangeably used for the limited numbers of the connection parts 204d of the main body 210a so that the problem of space of the main body and increase of the number of tubes can be solved.

On the other hand, similarly in this case, mounted instruments are required to be specified. In this case, plural identification pins 205a are provided for the connection parts 204a–204c of the tubes and correspondingly identification bushes 205b for inserting the identification pins 205a are provided for the connection parts 204d of the main body 210a.

The identification pins 205a provided for the tube are bridge connected in different manners corresponding to the kinds of the instruments and a logic element is connected between the identification bushes 205b of the main body 210a. Therefore, plural logic elements are connected in different manners by connecting different instruments to the connection parts 204d of the main body 210a and fitted instrument is specified by its output signals. JP-B-6-9577 proposes a medical apparatus in which instruments are detachably and exchangeably fitted to the medical apparatus by means of a multi joint connection as shown in. FIG. 19.

The dental apparatus 300 is provided with a main body 350 and a tube 310 introduced from the main body. A multi joint connection 311 is provided for the tip end of the tube 310 and several instruments 301a–301e, such as a micro motor handpiece, an air turbine handpiece, and scaler, are designed to be detachably and exchangeably attached to the connection part 311.

The main body 350 has a control part 330, an identification and command circuit 340 and a switch circuit 341. The control part 330 has an operation power supply circuit 320 for supplying electric power, a water supply circuit 321 for supplying water, a chip air supply circuit 322 for supplying cooling air, and a drive air supply circuit 323 for supplying drive air to an air turbine handpiece and so on corresponding to the instrument. Required power, water, and air are supplied to the instruments 301a–301e fitted to the tube 310 from these circuits 320–323.

A power source 352 is connected to the operation power supply circuit 320, a water source 353 is connected to the water supply circuit 321, and an air source 354 is connected to the chip air supply circuit 322 and the drive air supply circuit 323.

The switch circuit 341 switches the operation power supply circuit 320 and the identification and command circuit 340 to be connected to an electric line 312 connected to the connection part 311 through the tube 310. The identification and command circuit 340 identifies which instrument is connected based on the difference of resistance and impedance of the instruments 301a–301e connected to the connection part 311 by the electric line 312 and gives a selection command for the power, water, and air required for the connected instruments depending on the identification results to the circuits 320–323.

Namely according to the dental apparatus 300, the fitted instrument is specified by measuring its electric characteristic inherent to the instruments 301a–301e without providing separate resistance or wiring for the instruments 301a–301e for identification.

A water line 313 from the water supply circuit 321, a chip air line 314 from the chip air supply circuit 322, and a drive air line 315 from the drive air supply circuit 323 are provided in the tube 310 other than the electric line 312 and reach to the connection part 311. Sensor means 316 for detecting attachment and detachment of the instrument is provided in the connection part 311 of the tube 310.

The dental apparatus 300 is also provided with a drive control switch 351 for supplying power, water, and air to the connected instruments 301a–301e to be driven and the signals of the switch 351 are sent to the control part 330 and the identification and command circuit 340.

According to the dental apparatus 300, when any one of instruments is connected to the connection part 311 of the tube 310, its connection is detected by the sensor means 316, the switch circuit 341 is switched to the identification and command circuit 340, and the circuit 340 identifies the connected instrument and stores its result.

Then, when the drive control switch 351 is operated, the switch circuit 341 is switched to the operation power supply circuit 320, a command is sent for each supply circuit 320–323 based on the identification result of the instruments stored in the identification and command circuit 340, and required power, water, air are supplied.

According to such construction, plural instruments 301a–301e can be attached detachably and exchangeably on one tube 310 and correspondingly required power, water, and air can be supplied so that the same effect as FIG. 17 and FIG. 18 can be achieved.

However in FIG. 17, FIG. 18, and FIG. 19, identification signals aren't actively sent from the instruments. The main body requires measuring means such as the identification and command circuit 340 and the switch circuit 341 of the apparatus 300 in FIG. 19. Additionally, for example, it requires to; a) generate an accurate voltage, b) apply the voltage to the instrument, c) detect the electric current, and d) measure resistance value and specify the instrument, for measuring the resistance of the instrument. Especially c), detect the electric current, is troublesome operation and improvement has been desired.

Further, the resistance and the impedance used as identification means of the instrument in FIG. 17 and FIG. 19 are passive elements and analog elements which can't actively generate signals by themselves, they can't be used when they get wet and its secular change can't be ignored. Therefore, they can't identify precisely so that they can't identify the particular instrument although they can identify the kinds of the instruments when there are plural members of the same kinds of instruments.

On the other hand in case of FIG. 19 in which an instrument is constructed as a bridge medium with different logic elements provided for the main body, the above-mentioned secular change isn't caused, but the numbers of the identification pins 205a and the identification bushes 205b are required to be increased corresponding to the number of the kinds of the instrument. Therefore, there has been a problem such that the connection part 204 is enlarged and complicated.

Further in any of the cases of FIG. 17, FIG. 18, and FIG. 19, instruments are considered as; passive members of the main body and aren't considered as active members which operate actively and independently.

SUMMARY OF THE INVENTION

The present invention has been proposed in view of the above-mentioned problems. It is an object of the present invention to provide an identification type instrument which is easily and surely specified by the main body by actively generating self-identification signals, wherein a problem of increase of the kinds of instrument is solved and independent control of the instrument itself can be done, and to provide an identification type tube, an identification type adapter, and a medical apparatus using them.

The new terms such as an instrument assembly used in the present invention are explained.

An instrument assembly means an instrument itself, a combination of an instrument and an adapter, or a combination of an instrument and a tube according to circumstances. The reason for suggesting such term is as follows.

The object of the present invention is to specify an instrument connected to a main body. Therefore, its largest characteristic is in that identification signal output means for actively outputting unique identification signals specifying an instrument for the instrument detachably connected to the main body. In this case, even if the position housing the identification signal output means is the instrument itself, if the instrument and the main body are connected with a tube, the position may be at the tube. Further, an adapter incorporating the identification signal output means may be interposed between the tube and the instrument.

Accordingly, the subject to specify the instrument is the instrument itself, the instrument and the adapter, or the instrument and the tube according to the position where the identification signal output means is housed when seen from the main body. It is because specifying of the instrument can't be done without them when the identification signal output means is housed in the adapter or the tube.

The identification type instrument which is provided with the identification signal output means and can be specified by the main body when fitted on the main body detachably must have the identification signal output means. If the identification signal output means is housed in the adapter, the instrument is required to be defined to include the adapter. And if the identification signal output means is housed in the tube, the instrument is required to be defined to include the tube. On the other hand, a conventional instrument doesn't generally include the adapter and the tube, therefore, it maybe confused if the instrument is used as the one including the adapter and the tube.

Therefore, in the present invention, the term instrument assembly is newly proposed and the content is defined as mentioned above.

Accordingly, the original content of the instrument assembly includes all instruments for diagnosis or treatment by means of only electricity or water and air other than electricity like the conventional instrument and its applying means such as electricity isn't limited. Further, it may include instruments which do not use electricity. For example, it may include an instrument for cutting and grinding by electric drive means, for spraying and discharging clean water or drug solution, for treating by electric action, and for measuring voltage and current by a combination of a certain electric contact for diagnosis. In dentistry, an instrument assembly includes a handpiece, an air turbine handpiece, a micro motor handpiece, a scaler, photo polymerization means, a measuring device of root canal length, an intraoral camera, a pocket measuring device, a root canal filler, and a root canal treatment device.

The connection method of the instrument to the main body isn't limited by a tube and includes the manner such that the instrument assembly has a self drive source and is wirelessly connected with the main body.

The medical apparatus includes all the apparatus wherein the instrument assembly is connected to the main body via the tube or the adapter and diagnosis and treatment are executed by supplying power, water, and air to the instrument assembly and includes dental apparatus such as a dental unit and treatment apparatuses used in the field of otolaryngology, gynecology, urology, ophthalmology, and so on.

The detachable connection between the instrument assembly and the treatment apparatus includes multi joint connection and others.

An identification type instrument assembly is proposed at first, an identification type adapter is proposed secondly, an identification type tube is proposed later, and a medical apparatus using these identification type instrument assembly, adapter, and tube is proposed finally.

The identification type instrument assembly, adapter, and tube of the present invention aren't passive like the prior art and are characterized in that they house active identification signal output means for positively sending out self identification signals. The instrument assembly isn't considered as a passive member like the prior art, is considered as an active or independent member, sends out self identification signals by itself, and further is provided with self control ability.

In other words, the instrument assembly and so on are constructed as a member having a predetermined control ability respectively and for sending out self identification signals, not a tail end of a central processing system having control function only in an main body, so that a more flexible and higher adaptable distributed processing system can be constructed as the entire apparatus providing these instrument assembly and so on. Further according to this method, connection isn't limited to tubes and wireless connection is possible so that it can easily correspond to multi joint connection.

The inventors of the present invention adequately understand miniaturization of integrated circuit and its characteristic as a digital equipment, have found that micro-mini integrated circuit can be housed in an equipment in which space is limited such as dental instrument assembly, which has been considered to be impossible to embed active identification signal output means in prior art, and also have reached the present invention so as to utilize its active function and its digital function.

According to the first embodiment of the present invention, the identification type instrument assembly detachably connected to the main body of the medical apparatus for use in diagnosis and treatment, is characterized in that the instrument assembly has an identification signal output means for actively outputting self-identification signals prepared in advance under a predetermined procedure.

The instrument assembly is characterized in having the identification signal output means as the above-mentioned active element and the main body provided with the instrument assembly can specify the instrument assembly only by reading the identification signals output from the output means so that the read means in the whole main body can be simplified.

In this case, it isn't important that the connection of the instrument assembly and the main body is multi joint connection or not. If it is multi joint, it is indispensable to specify the kinds of the fitted instrument assembly and the identification signal output means is considered to the specifying means.

However, the active identification signal output means can also communicate signals wirelessly and transmit digital signals as identification signals, so that it can specify the instrument assembly in more detail, namely it can specify not only its kind but also its individuality. If the instrument assembly and the main body are connected by a tube or exclusive connection means, the output means can bring out advantages which haven't been seen in prior art.

For example, the instrument assembly and the main body are connected by an exclusive tube and individual specifying of the same kind of instrument assembly is possible, the main body can manage a record of use of each instrument assembly, distinct old and new, and distinct using operator, so that minute control can be possible.

In the identification type instrument assembly for use in diagnosis and treatment by detachably connecting to the main body of medical apparatus as the second embodiment, it is characterized in that the instrument assembly is comprised of an instrument and an adapter detachably fitted to the instrument for connecting the instrument assembly to the main body and the adapter houses identification signal output means for actively outputting self-identification signals prepared in advance under a predetermined procedure.

According to the instrument assembly, comparing to that of the first embodiment, the location of the identification signal output means is limited to the adapter which is able to be detachable from the instrument assembly, and the instrument assembly is defined to include the adapter.

The same effect as the first embodiment can be achieved and also the instrument assembly can be autoclaved by removing the adapter even if the identification signal output means doesn't have resistance to autoclave, when the identification signal output means is provided for the adapter.

In the third embodiment, the identification type instrument assembly detachably connected to a main body of a medical apparatus for use in diagnosis and treatment is characterized in that the instrument assembly is comprised of an instrument and a tube detachably fitted to the instrument assembly for connecting the instrument assembly to the main body and the tube houses identification signals output means for actively outputting self-identification signals prepared in advance under a predetermined procedure.

According to the instrument assembly, comparing to that of the first embodiment, the location of the identification signal output means is limited to the tube which is detachable from the instrument assembly, and the instrument assembly is defined to include the tube.

The same effect as the first embodiment can be achieved and also the instrument assembly can be autoclaved by removing the tube even if the identification signal output means doesn't have resistance to autoclave, when the identification signal output means is provided for the tube.

In fourth embodiment the identification type instrument is characterized in that the identification signal output means is comprised of an ID code output element for serially outputting the ID code proper to the instrument assembly as identification signals.

In this embodiment, the identification signal output means is specifically defined as the ID code output element, and the instrument assembly can be specified by executing serial communication with the ID code output element in the main body. The identification signal output means can be constructed as the simplest one.

In fifth embodiment the identification type instrument assembly is characterized in that the identification signal output means is comprised as a microcomputer element or a communication integrated element.

In this instrument assembly, the identification signal output means is specifically defined as a microcomputer element or a communication integrated element. The main body can specify the instrument assembly by communicating these elements, and the instrument assembly can be controlled independently. On the other hand in the main body, a predetermined control is transferred to the instrument assembly and a distributed processing system can be constructed.

In sixth embodiment the identification type instrument assembly is characterized in that the identification signal output means is provided with nonvolatile storage means and serial data, voltage level signals amplitude is varied at a predetermined repetition cycle, and frequency identification signals of whose frequency is varied are used as the identification signals based on the data stored in the nonvolatile storage means.

In the instrument assembly, a generation method of identification signals of the identification signal output means and embodiment of the identification signals are defined, and signals are defined as digital signals or signals capable of being digitized, so that the instrument assembly having the same effect as the first to third embodiment can be easily achieved.

The identification type instrument assembly described in the 7-th embodiment is characterized in that a connection part for detachably connecting the instrument assembly to the main body is a multi joint connection.

The multi joint connection means connection in which plural kinds of different instrument bodies are connected to a single connection, or to any of a plural connections provided for the main body as explained in prior art. The location of the connection isn't limited and there is a case that it is directly provided for the main body or it is provided at the tip end of the tube from the main body depending on the content of the instrument assembly.

When the instrument assembly and the main body are thus connected by the multi joint connection, it is especially important to specify the connected instrument. Active identification signal output means can easily and surely specify the instrument and facilitate the equipment construction of the main body.

Particularly in these years, medical apparatus is often provided with microcomputer elements as control means. In such a case the signals from the identification signal output means is read by the control means with suitable software and the instrument assembly is specified without providing separate analog identification means as explained in the prior art.

In the identification type instrument assembly of the 8-th embodiment, the instrument assembly is comprised of an instrument and an adapter detachably fitted to the instrument and is capable of detachably connecting to a tube from the main body via the adapter, the identification signal output means is provided for the adapter, and connection between the adapter and the tube is a multi joint connection.

In such an instrument assembly, the location of the multi joint connection in the 7-th embodiment is defined between the adapter provided for the instrument assembly and the tube like the second embodiment. The same effect as the second embodiment in addition to the same effect as the 7-th embodiment can be achieved.

In the identification type instrument assembly of the 9-th embodiment the instrument assembly is comprised of an instrument and a tube detachably fitted to the instrument and is capable of detachably connecting to the main body via the tube, the identification signal output means is provided for the tube, and connection between the tube and the main body is a multi joint connection.

In such an instrument assembly, the location of the multi joint connection in 7-th embodiment is defined between the tube provided for the instrument assembly and the main body like the third embodiment. The same effect as third embodiment in addition to the same effect as the 7-th embodiment can be achieved.

The identification type adapter detachably fitted for an instrument assembly for use in diagnosis and treatment by detachably connecting to the main body of medical apparatus of the 10-th embodiment is characterized in that the adapter is provided with identification signal output means for actively outputting unique self-identification signals prepared in advance for identifying the instrument assembly under a predetermined procedure, and the connected instrument assembly can be specified in the main body by the identification signals output from the identification signal output means when the instrument assembly having the adapter is connected to the main body.

According to such an adapter, the adapter provided for the identification type instrument assembly as the second embodiment is defined as a separate one. The same effect as the second embodiment can be achieved by detachably fitting the adapter between the instrument assembly without having the identification signal output means and the main body.

The identification type adapter of the 11-th embodiment is characterized in that a connection part for detachably connecting the adapter to the main body is a multi joint connection.

According to such an adapter, the adapter provided for the identification type instrument assembly as the 8-th embodiment is defined as a separate one. The same effect as the 8-th embodiment can be achieved by detachably fitting the adapter by means of a multi joint connection between the instrument assembly without having the identification signal output means and the main body.

The identification type tube of the 12-th embodiment is a tube connecting an instrument assembly and the main body of medical apparatus for use in diagnosis and treatment by detachably connecting to the main body of medical apparatus and is characterized in that the tube is provided with identification signal output means for actively outputting unique self-identification signals prepared in advance for identifying the connected instrument assembly under a predetermined procedure, and the connected instrument assembly can be specified in the main body by the identification signals outputted from the identification signal output means when the instrument assembly is connected to the main body via the tube.

According to such a tube, the tube provided for the identification type instrument assembly as the third embodiment is defined as a separate one. The same effect as the third embodiment can be achieved by detachably fitting the adapter between the instrument assembly without having the identification signal output means and the main body.

The identification type tube of the 13-th embodiment is characterized in that a connection part for detachably connecting the tube to the main body is a multi joint connection.

According to such a tube, the tube provided for the identification type instrument assembly as the 9-th embodiment is defined as a separate one. The same effect as the 9-th embodiment can be achieved by detachably fitting the adapter by means of a multi joint connection between the instrument assembly without having the identification signal output means and the main body.

The medical apparatus of the 14-th embodiment is for use in diagnosis and treatment by detachably connecting plural instrument bodies to the main body and is characterized in that the instrument assembly is comprised as identification type instrument assembly having identification signal output means for actively outputting self-identification signals prepared in advance under a predetermined procedure, and the connected instrument assembly can be specified in the main body by the identification signals output from the identification signal output means when the instrument assembly is connected to the main body.

Such a medical apparatus corresponds to the identification type instrument assembly of the first embodiment, and the same effect as the first embodiment can be achieved.

The 15-th embodiment is characterized in that a drive circuit or a control circuit corresponding to the specified instrument assembly can be automatically connected to the instrument assembly.

Such a medical apparatus defines corresponding action of the main body after specifying the instrument assembly. After specifying, the drive circuit or the control circuit of the main body automatically corresponds to the specified instrument assembly. Therefore, an operator can concentrate on medical examination because he only fits the instrument assembly to the main body without setting the drive circuit of the apparatus according to the fitted instrument, thereby it is convenient.

According to the medical apparatus of the 16-th embodiment, the medical apparatus is characterized in that the display mode of display means and/or input mode of input means such as a touch panel can be automatically switched corresponding to the specified instrument assembly when the instrument assembly is specified.

According to such a medical apparatus, either the mode of the display means or the mode of the input means or both of them can be switched so as to correspond to the attached instrument assembly other than switching the drive circuit, so it is further convenient for the operator.

According to the medical apparatus of the 17-th embodiment, the medical apparatus is characterized in that management of usage history and distinction of using operator of the specified instrument assembly can be executed when the instrument assembly is specified.

The medical apparatus positively utilizes the advantage that not only the kind of the instrument assembly but also the individuality of the instrument assembly can be specified by the identification signals outputted from the identification signal output means as the first embodiment, thereby more minute control of the instrument assembly can be executed.

According to the medical apparatus of the 18-th embodiment, the medical apparatus is characterized in that the main body is provided with a microcomputer element or a communication integrated element as identification means of identification signals output from the identification signal output means of the connected instrument assembly.

According to such a medical apparatus the identification means of the identification signals outputted from the instrument assembly is defined. Because the identification signal output means of the instrument assembly actively outputs identification signals, the microcomputer element or the communication integrated element can be provided as the identification means for the main body, and construction of the apparatus can be facilitated. Further, if the microcomputer element and so on is provided as the control means for the main body, suitable software can realize the identification.

According to the medical apparatus of the 19-th embodiment, the medical apparatus is characterized in that wiring of the connection part detachably connecting the instrument assembly with the main body is a tree structure.

Such a medical apparatus has the advantage that because the connected instrument actively outputs identification signals, its pathway doesn't affect specifying of the instrument assembly. The connection to the connection part of the instrument assembly can be tree wiring, not separate wiring like in the prior art, so that wiring of the main body can be simplified.

According to the medical apparatus of the 20-th embodiment, the medical apparatus is, characterized in that the instrument assembly is the identification type instrument assembly as the first to 9-th embodiment, and/or is the instrument assembly connected via the identification type adapter as the 10-th or 11-th embodiment, and/or the instrument assembly connected via the identification type tube as the 12-th or 13-th embodiment.

According to such a medical apparatus, it is defined that the medical apparatus as any one of the 14-th–19-th embodiment corresponds to the identification type instrument assembly as the first to 9-th embodiment, the instrument assembly connected via the identification type adapter as the 10-th or 11-th embodiment, or the instrument assembly connected via the identification type tube as the 12-th or 13-th embodiment. Effects of the relating embodiment are synergistically achieved.

BRIEF DESCRIPTION OF THE DRAWINGS

FIG. 12 shows other embodiment of the medical apparatus having the identification type instrument assembly of the present invention, FIG. 12($a$) is its entire perspective view, and FIG. 12($b$) is a display sample of the display means.

DETAILED DESCRIPTION OF THE INVENTION

Figure 1:
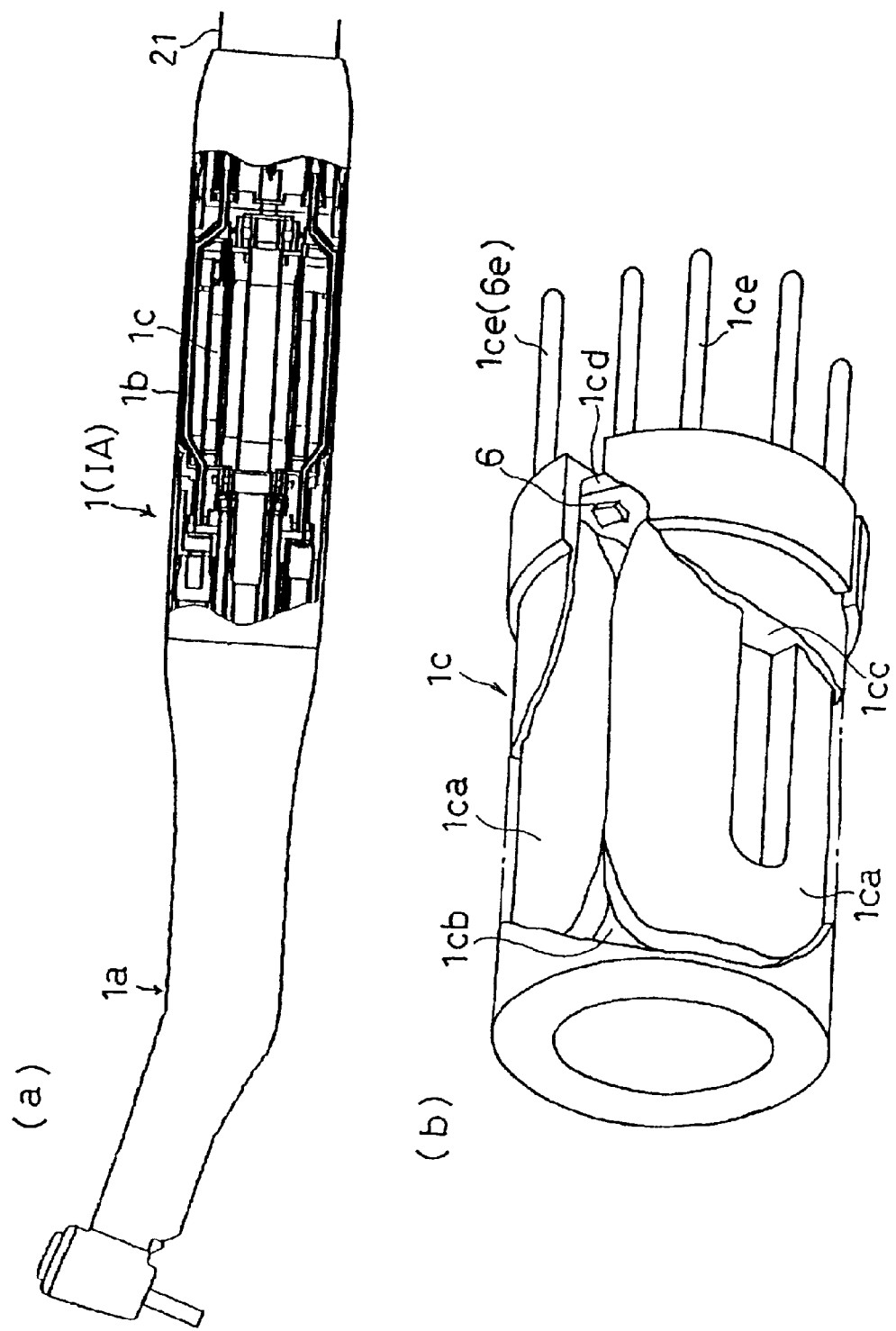
FIG. 1 shows one embodiment of the identification type instrument assembly of the present invention, FIG. 1(*a*) is a partially cutaway outline view and FIG. 1(*b*) is a partially cutaway outline view of the substantial part.

The preferred embodiments of the present invention are explained referring to the drawings. An instrument assembly, an adapter, a tube, and a medical apparatus for dental use are explained as an example, however, the present invention isn't limited to them as mentioned above.

Figure 2:
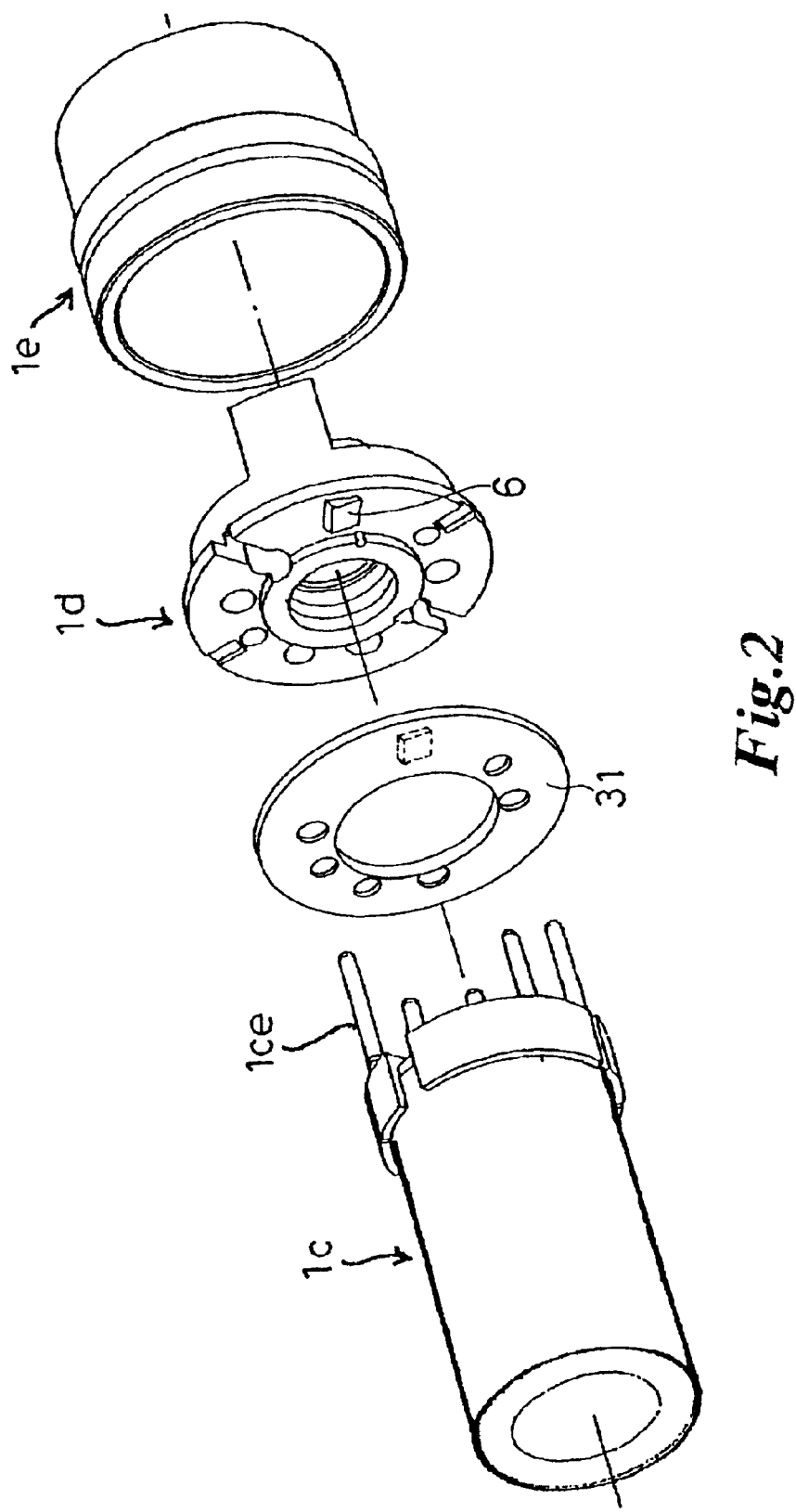
FIG. 2 is an exploded perspective view of the substantial part of the other embodiment of the identification type instrument assembly of the present invention.

FIG. 1 shows one embodiment of the identification type instrument assembly of the present invention, FIG. 1($a$) is a partially cutaway outline view and FIG. 1($b$) is a partially cutaway outline view of the substantial part. FIG. 2 is an exploded perspective view of the substantial part of the other embodiment of the identification type instrument assembly of the present invention.

The installation method of the identification signal output means which is a characteristic of the present invention is explained referring to these drawings.

The identification type instrument assembly 1 in FIG. 1 is a micro motor handpiece, comprised of a tool holder 1$a$ with a cutting tool at its tip end, detachable from the main part 1$b$, the main part 1$b$ housing a small motor, and the main part 1$b$ is connected to the main body (not shown) of the medical apparatus by a tube 21. The instrument assembly is a type (IA) constructed within the instrument 1 itself In this embodiment, identification signal output means 6 is housed in a stator 1$c$ of the small motor housed in the main part 1$b$ and its detail is shown in FIG. 1($b$).

The stator 1$c$ has a coil 1$ca$ around an inner cylinder 1$cb$ and is integrally formed by coating and molding with resin 1$cc$ together with a board 1$cd$ fitting these control members. A connection terminal 1$ce$ is extended from the board 1$cd$. In this figure, one part of the coating is broken to show the board 1$cd$ and the coil 1$ca$. The minute identification signal output means 6 is provided on the board 1$cd$ together with other control members and integrally coated and molded with resin. Some of the connection terminals 1$ce$ are used as a connection terminal 6$e$ for the identification signal output means 6.

Thus, the identification signal output means 6 is preferably housed in the instrument assembly 1 from the first. Further in this case, the identification signal output means 6 is integrally coated with resin and isn't affected by the outer environment so that its performance is safely achieved.

FIG. 2 shows other method for housing the identification signal output means in the instrument assembly constructed as the micro-motor handpiece like FIG. 1.

The stator 1$c$ of the small motor housed in the main part 1$b$ of the instrument assembly 1 is housed in the main part 1$b$ through a bracket 1$d$ and a ring 1$e$ at the connection terminal 1$ce$ side. An adapter 31 is interposed between the stator 1$c$ and the bracket 1$d$ and the identification signal output means 6 housed in the bracket 1$d$ is held and guarded by the protect ring 31.

In this way, the identification signal output means can be housed in the instrument assembly in which the identification signal output means isn't originally housed.

Figure 3:
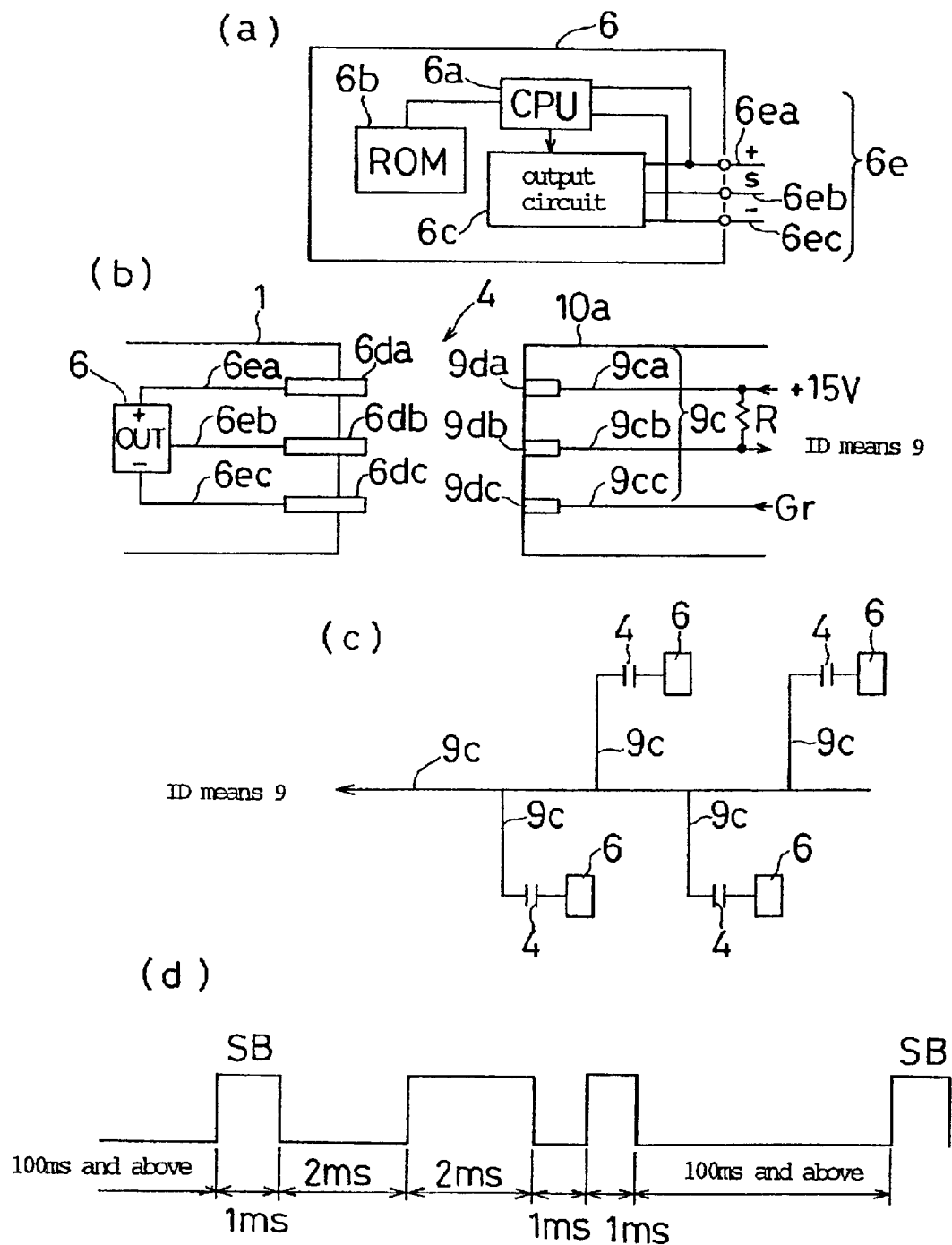
FIG. 3 explains the identification signal output means used for the identification type instrument assembly of the present invention, FIG. 3(*a*) is a block diagram showing its construction conceptually, FIG. 3(*b*) is a conceptual diagram showing connection of the main body and the signals, FIG. 3(*c*) is a conceptual diagram showing tree construction of the main body for connecting the identification signal output means, and FIG. 3(*d*) is a time chart showing one embodiment of the identification signals output from the identification signal output means.
Figure 4:
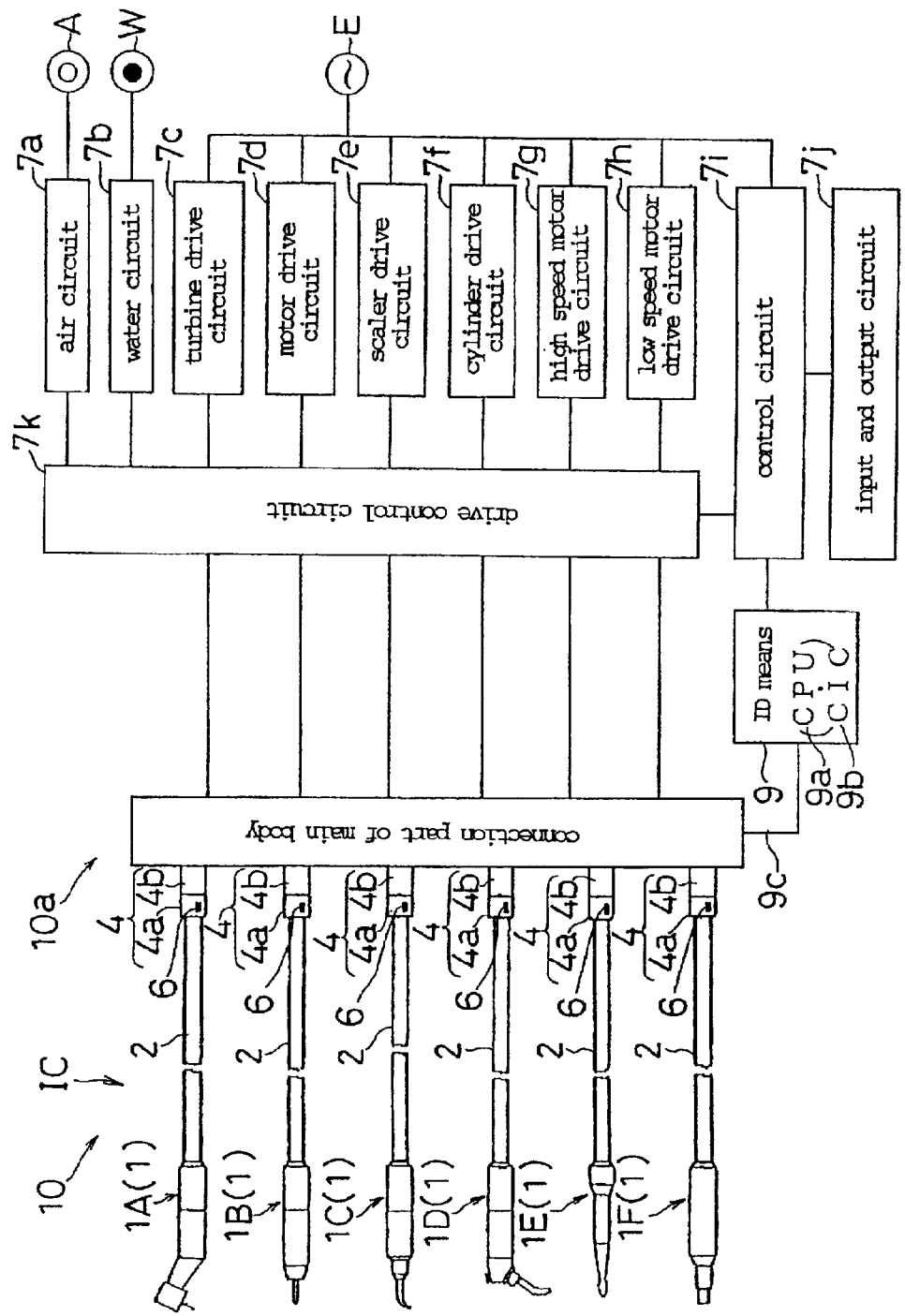
FIG. 4 is a block diagram conceptually showing one embodiment of the medical apparatus having the identification type instrument assembly of the present invention.

FIG. 3 explains the identification signal output means used for the identification type instrument assembly of the present invention, FIG. 3($a$) is a block diagram showing its construction conceptually, FIG. 3($b$) is a conceptual diagram showing connection of the main body and the signals, FIG. 3($c$) is a conceptual diagram showing tree construction of the main body for connecting the identification signal output means, and FIG. 3($d$) is a time chart showing one embodiment of the identification signals output from the identification signal output means. FIG. 4 is a block diagram conceptually showing one embodiment of the medical apparatus having the identification type instrument assembly of the present invention.

Details and basic function of the identification signal output means are explained referring to these drawings. The same numerals are allotted for the same members which have been already explained and their explanations are omitted.

The identification signal output means 6 in FIG. 3($a$) is one embodiment of the identification signal output means of the present invention and is comprised of CPU 6$a$ for controlling the entire output means 6, ROM (nonvolatile storage means) 6b for storing data required for control, an output circuit 6c operable by receiving instructions from the CPU 6a, and a connection line comprised of an electric source line 6ea, a signal line 6eb, and a common line 6ec.

The identification signal output means 6 is housed in the identification type instrument assembly 1 as shown in FIG. 3(b) and connection terminals 6da, 6db, and 6dc corresponding to respective connection line 6e are provided for the instrument assembly 1. The instrument assembly 1 is detachably fitted to the main body 10a.

Terminal receivers 9da, 9db, 9dc are provided for the main body 10a corresponding to the connection terminals 6da, 6db, 6dc of the instrument assembly 1. These terminal receivers 9da, 9db, 9dc are connected to the electric source line 9ca, the signal line 9cd, and the common line 9cc and a resistance R is bridged between the electric source line 9ca and the signal line 9cb.

These electric source line 9ca, a signal line 9cb, and a common line 9cc are collectively called the connection line 9c of the main body. The signal line 9cb is connected to the identification means 9 (see FIG. 4) provided for the main body. In this embodiment, the connection between the instrument assembly 1 and the main body 10a is called an instrument connection 4.

Thus, when the instrument assembly 1 is fitted to the main body 10a, the connection terminals 6da, 6db, 6dc of the instrument assembly 1 and the connection receivers 9da, 9db, 9dc of the main body 10a are connected, electric source (5V direct current in this embodiment) is supplied from the main body, the CPU 6a of the identification signal output means 6 detects the supply. Unique self identification signals prepared in advance for identifying the instrument assembly 1 are read out from the ROM 6b and is output from the signal line 6eb through the output circuit 6c, and the identification means 9 receives the identification signals by the signal line 9db and specifies the instrument assembly by simply reading the signal or by communicating with the identification signal output means 6.

The identification signal output means 6 can be constructed from CPU 6a of the most simple type as an ID code output element which, by receiving electric source from the main body, serially output an ID code proper for the instrument body 1 as identification signals. In such a case the construction of the identification signal output means is most simple.

However, the identification signal output means 6 can construct the CPU 6a as a more advanced microcomputer element or communication integrated element. In such a case, the instrument assembly can be controlled more independently and the main body can transfer a predetermined control to the instrument assembly and a distributed processing system can be constructed.

The identification signals are read out and output from the ROM (nonvolatile storage means) 6b and its embodiment includes not only the above-mentioned serial data but also voltage level signals of which amplitude is varied at a predetermined repetition cycle and frequency identification signals of which frequency is varied.

The identification signal output means 6 actively outputs identification signals so that the pathway of the signals doesn't have an affect on specifying of the instrument assembly. When plural instrument connections 4 are provided, the connections can be a tree structure wiring like FIG. 3(c) and wiring of the main body can be simplified unlike the conventional separate wiring.

A communication method when the connections to the instrument connections 4 are tree structure wiring, an ID code output element is used as the identification signal output means, and ID code which is serial data is outputted as identification signals is explained in more detail also referring to FIG. 3(d).

Because the signal line 6eb is always "H" when nothing is connected to the main body 10a, the identification means 9 detects it as non connected and executes a non connection display.

When the instrument assembly 1 housing the identification signal output means 6 is connected, the power source is supplied from the main body 10a and serial data shown in FIG. 3(d) is output in the identification signal output means 6. The data is comprised of a combination of "L" 100ms and above, "H" of 1ms or "L", or "H" of 2ms or "L" and sends 6 bit code (001101B) per 1ms. The signal "H" of 1ms next to the "L" 100ms and above is defined as a start bit SB.

The identification signal output means 6 continuously outputs such serial data, the identification means 9 of the main body 10a samples the received data per 1ms, detects the data, reads the ID code of the connected instrument assembly 1, and specify the instrument assembly 1.

FIG. 4 shows a medical apparatus 10 wherein six different kinds of identification type instrument assembly (1A–1F) are connected to the main body 10a via each exclusive tube 2. The instrument assembly is a type IC in which the instruments 1A–1F are combined with the tubes 2 respectively.

The kinds of the instrument assembly IC, namely the instrument assembly 1, are a turbine handpiece 1A, a motor handpiece 1B, a scaler 1C, a three-way cylinder 1D, a high speed motor handpiece 1E, and a low speed motor handpiece 1F. Each tube 2 is connected to respective exclusive connection 4b provided for the main body 10a via a connection part 4a at tube side. Namely the medical apparatus 10 doesn't correspond to a multi joint connection.

The main body 10a includes an air circuit 7a for supplying air required for the instrument assembly IC by receiving compressed air from an air source A, a water circuit 7b for supplying water required for the instrument assembly IC by receiving water from a water source W, a turbine drive circuit 7c, a motor drive circuit 7d, a scaler drive circuit 7e, a cylinder drive circuit 7f, a high speed motor drive circuit 7g and a low speed motor drive circuit 7h, all circuits supplying drive power source depending on the kinds of the connected instrument assembly IC (1A–1F) by receiving power supply from an outer electric source E, a control circuit 7i controlling the entire apparatus, output means (not shown) such as a liquid crystal display and a printer, and input means (not shown) such as a touch panel or a foot controller. It is also provided with the identification means 9 for distinguishing the identification signals output from the connected identification type instrument assembly IC in addition to an input and output circuit 7j for controlling the means and a drive control circuit 7h mentioned later.

The drive control circuit 7k connects and disconnects the drive circuits 7c–7h provided corresponding to the instrument assembly IC (1A–1F) one by one and switches to connect the air circuit 7a and the water circuit to the instrument assembly IC (1A–1F) if necessary.

In this embodiment, the housed position of the identification signal output means 6 in the instrument assembly IC is detected. Namely, the instrument assembly IC is considered to include the tube 2 and the connection 4a and the identification signal output means 6 is housed in the end of the tube 2, that is at the connection 4a at tube side, not in the instrument 1A–1F.

In case of type IC, the instrument 1 is usually detachable to the tube 2 and the instrument 1 can be autoclaved by removing from the tube if required, therefore there is no problem if the identification signal output means 6 doesn't have resistance to being autoclaved.

Next, the role of the identification signal output means 6 which is connected to the main body 10a by the exclusive connection 4, has respective drive circuit, and doesn't correspond to multi joint connection is explained.

The identification signal output means 6 can be constructed as the ID code output means as explained in FIG. 3, the ID code is allotted as an individual production number of each ID code output means, so that the output means 6 can specify not only the kind of the housed instrument but also the individual instrument. Accordingly all of each instrument assembly IC can be distinguished.

Therefore, individual record management of each instrument assembly such as frequency in use, integrated time of use, and frequency of trouble is executed, and warning is given for the instrument which has been used over the predetermined time or such instrument may be made impossible to be used by controlling connection and disconnection of the drive control circuit 7k. Further, an exclusive instrument is set for each operator and a warning may be given or the instrument is made impossible to be used if an operator connects the other operator's instrument assembly by mistake.

Following is one sample of the record management table of the instrument assembly for executing the above-mentioned individual record management used in the control circuit 7i of the medical apparatus 10.

<Record management table of instrument assembly>

| ID code | kind | operator | previous used date | integrated use time | record |
|---------|------|----------|--------------------|--------------------|--------|
| A0101001 | TH | AA | 000630/1500-1600 | 500H30M | K0 |
| A0101021 | TH | BB | 000703/1000-1100 | 000H15M | K1 |
| B0202001 | MH | AA | 000630/1600-1620 | 1600H20M | K0 |
| C0303001 | SC | AA | 000620/1100-1110 | 1100H00M | K1 |

In this table "TH" in "kind" is a turbine handpiece, "MH" is a motor handpiece, "SC" is a scaler. In "previous used date" latest used date is shown in year, month, and date in two figures and start time and end time of the used time in 24-hour. In "integrated used time", the sum of the used time of the instrument assembly so far is shown in hour (H) and minute (M). In "record", several records in the past is shown as reference number, for example "K0" means there was no trouble and "K1" shows there was one trouble.

If such a management table is prepared for the apparatus 10 and is revised each time the instrument is used, the above-mentioned individual record management of the instrument assembly can be executed. Therefore, it can be prevented that an operator uses the other operator's instrument by mistake, limit time of usage is set and the instrument which is over this limit can be exchanged. In such a manner more minute usage control of the instrument assembly can be executed and it makes a contribution to more safe medical examination.

The identification signal output means actively outputs signals by itself, therefore, it can send and transmit signals between the instrument assembly and the main body in wireless, the number of the connection terminals of the connection can be reduced, and further the instrument assembly can be cordlessly constructed as a complete independent type.

Because the identification signal output means 6 of the instrument assembly IC actively outputs identification signals, CPU (microcomputer element) 9a or CIC (communication integrated element) 9b can be provided as the identification means 9 of the main body 10a so that the construction of the apparatus can be simplified. Further, if CPU (microcomputer element) is already provided for the control circuit 7i of the main body 10a, the CPU of the control circuit 7i can be also used as the identification means 9 by using a program having the function of the identification means.

Figure 5:
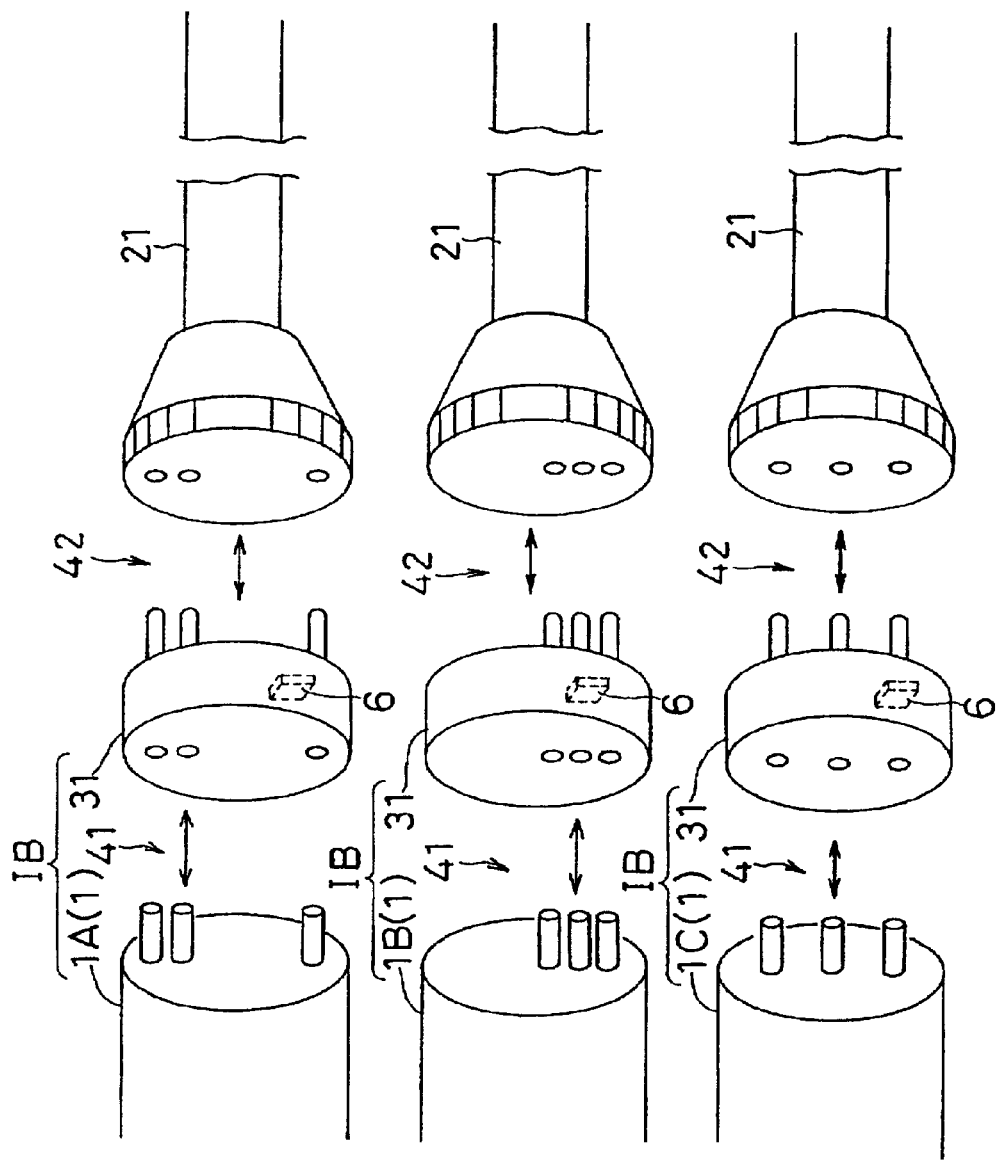
FIG. 5 shows other embodiment of the identification type instrument assembly of the present invention.

FIG. 5 is a conceptual diagram showing other embodiment of the identification type instrument assembly of the present invention. The instrument assembly is type IB in which an exclusive adapter housing each identification signal output means 6 is detachably fitted to several instruments 1A–1C.

The instrument assembly IB (1A–1C) and the main body are connected via each exclusive tube 21, the connection 41 between the instrument assembly 1A–1C and the adapter 3 and the connection between the adapter 31 and the tube 21 are connected by each exclusive connection terminal in 1 to 1. It isn't multi joint type connection.

The instrument assembly IB can be autoclaved if required by removing the instrument 1 from the adapter 31 like FIG. 4 so that if the identification signal output means 6 doesn't have resistance to being autoclaved, there is no trouble. Further, its individual record management can be executed like the instrument assembly IC in FIG. 4.

Figure 6:
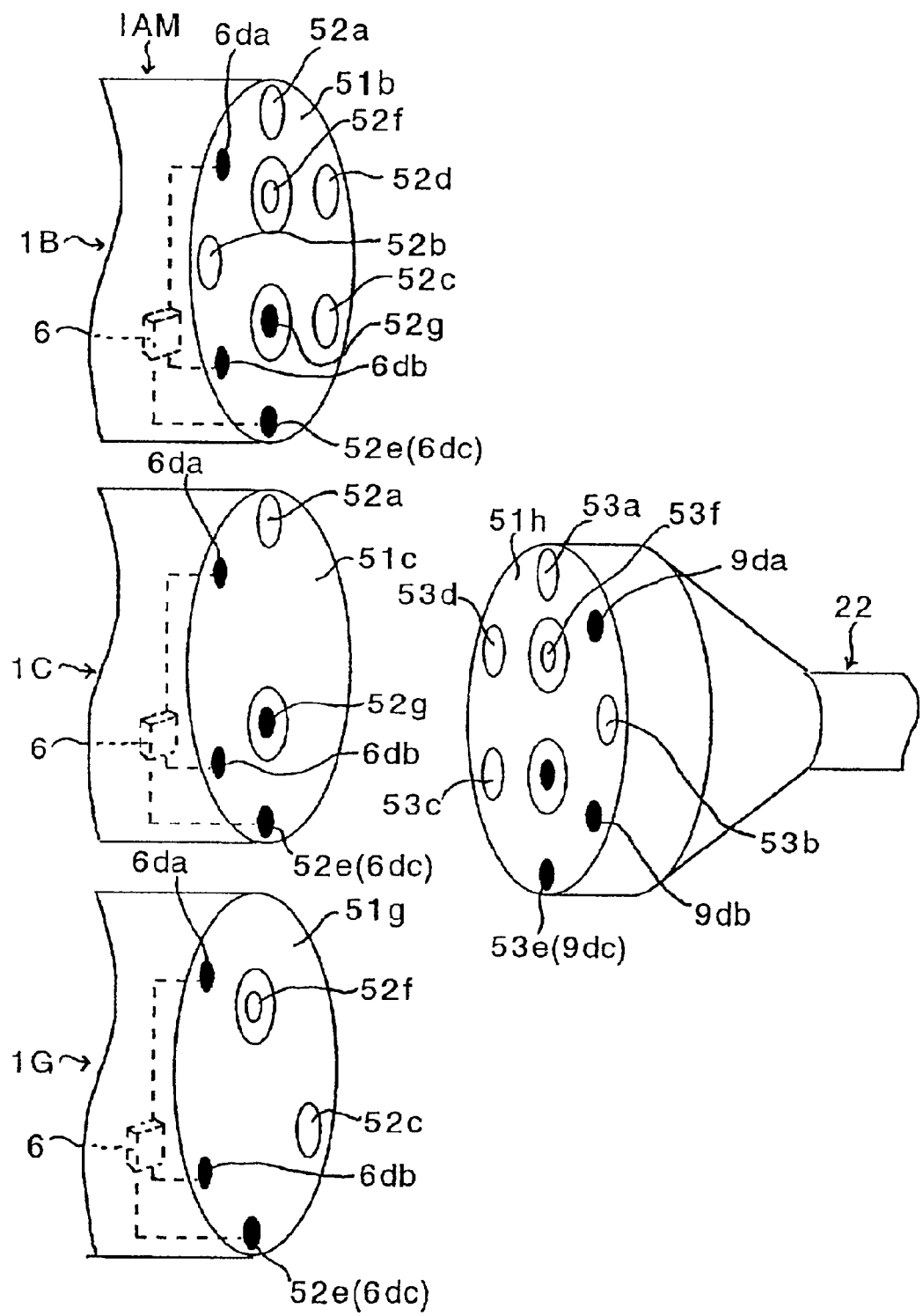
FIG. 6 shows one embodiment of the identification type instrument assembly of the present invention having multi joint connection.

FIG. 6 is a conceptual diagram showing one embodiment of the identification type instrument assembly of the present invention having multi joint connection. In FIG. 6 and FIG. 13–17, the terminal at the connection is shown as flat so as to conceptually show the positions and kinds of the terminal and its actual construction may be a combination of convex and concave like FIG. 5 or may be provided concentricity back and forth in the axial direction.

In the above-mentioned, the connection of the instrument assembly and the main body isn't limited to multi joint type connection. Hereinafter, embodiments of which connection corresponds to multi joint are explained.

Multi joint connection means a connection in which plural instrument bodies can be connected and used for either a single connection or any one of plural connections of the main body. In such a case it is required to specify which instrument assembly is connected to the multi joint connection and the identification type instrument assembly of the present invention especially brings out its effect.

In this embodiment, the connection of the tube 22 introduced from the main body 10a is constructed as a multi joint connection 51h and also connections 51b, 51c, 51g of the corresponding identification type instrument assembly 1B, 1C, 1G are constructed as multi joint connection. The instrument assembly is type IAM which is comprised of the instrument itself and the connection to the main body is a multi joint type.

The multi joint connection 51h of the tube 22 has a connection terminal for electricity, 53a, 53b, 53c, 53d, 53e, a connection terminal for air 53f, and a connection terminal 53g for water and further has the electric source connection terminal 9da and the connection terminal for signals 9da for identification, mentioned above. The connection terminal 53e of the connection terminals for electricity is a common line and functions as a connection terminal for common line 9dc for identification.

The appropriate numbers of the above-mentioned connection terminals are prepared and their positions are fixed in such a manner that the required electric source, water, and air can be supplied if any one of the instrument bodies IAM (1B, 1C, 1G) which is detachably used for the tube 22 is fitted.

The multi joint connection 51b, 51c, 51g of the instrument assembly IAM (1B, 1C, 1G) houses the identification signal output means 6 and corresponds to multi joint. The connection 51b of the instrument assembly IAM (1B) constructed as a motor handpiece has connection terminals 52a, 52b, 52c for a small three-phase motor, a connection terminal 52d for a lamp, a connection terminal 52e for a common line, a connection terminal 52f for air, a connection terminal 52g for water, and further an electric source connection terminal 6da for identification. The connection terminal for a common line 52e is similarly shared as 6dc.

The connection terminals 52a–52g, 6da–6dc of the instrument assembly are located at the same place as the connection terminals 53a–53g, 9da–9dc of the tube. Therefore, if the multi joint connection 51b of the instrument assembly IAM (1B) is connected to the multi joint connection 51h of the tube 22, the connection terminals of electric source, water, and air required for the instrument assembly 1B are connected and electricity, water and air are supplied.

The connection 51c of the instrument assembly IAM (1C) constructed as a scaler has a connection terminal for a scaler 52a, a connection terminal for a common line 52e, a connection terminal for water 52g. As for the connection terminals 6da, 6db, 6dc for identification are the same as the connection 51b of the instrument assembly IAM (1B).

The connection terminals 52a, 52e, 52g, 6da–6dc of the instrument assembly are located at the same place as the connection terminals 53a, 53e, 53g, 9da–9dc of the tube. Therefore, if the multi joint connection 51c of the instrument assembly IAM (1C) is connected to the multi joint connection 51h of the tube 22, the connection terminals of electric source, water, and air required for the instrument assembly 1C are connected and electricity, water and air are supplied.

The connection 51g of the instrument assembly IAM (1G) constructed as a photo polymerization means has a connection terminal for polymer lamp 52c, a connection terminal for a common line 52e, a connection terminal for air 52f. As for the connection terminals for identification 6da, 6db, 6dc are the same as the connection 51b of the instrument assembly IAM (1B).

The instrument 1B constructed as a motor handpiece, the instrument 1C constructed as a scaler, and the instrument 1G newly constructed as photo polymerization means as other embodiment among the six instruments 1A–1F shown in FIG. 4 are shown as a sample of the instrument assembly IAM. The reason is that they are appropriate as an embodiment in which selection of electric source, water, and air is different. If the connection is a multi joint corresponding type, the six instruments 1A–1F shown in FIG. 4 and other type instruments may be constructed as the instrument assembly IAM used by detachably connecting to the multi joint connection 51h of the tube 22.

The multi joint connection 51 comprised of the multi joint connections 51b, 51c, 51g of the instrument assembly and the multi joint connection 51h of the tube is thus constructed and can be detachably used for any instrument assembly. In such a case, it is important to specify the kind of fitted instrument assembly. The identification signal output means 6 housed in each identification type instrument assembly IAM (1B, 1C, 1G) outputs identification signals, the main body reads the identification signals or communicates with the identification signal output means 6 so that the connected instrument assembly is specified and the main body can correspond.

Figure 7:
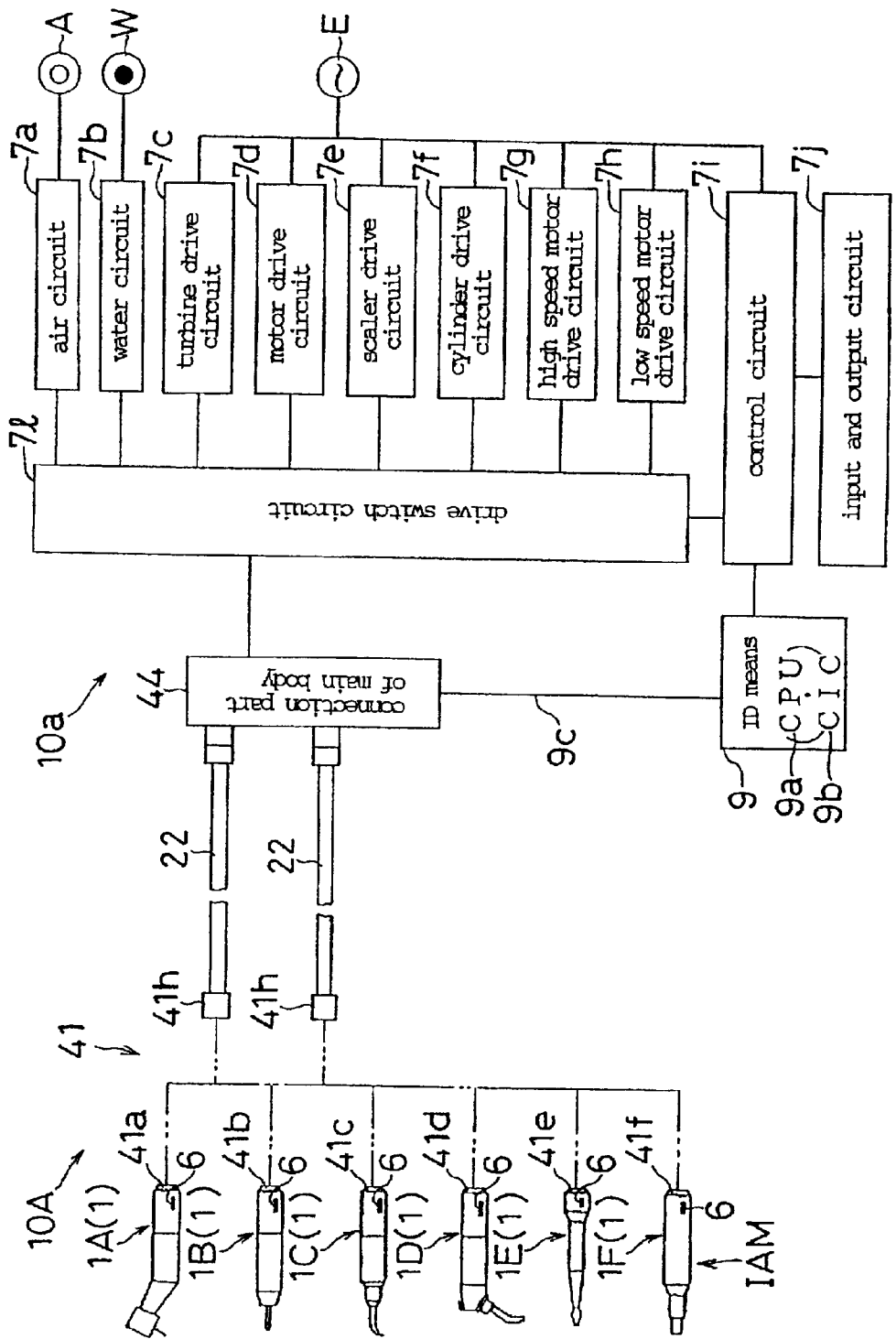
FIG. 7 is a block diagram conceptually showing one embodiment of the medical apparatus having the identification type instrument assembly in FIG. 6.

FIG. 7 is a block diagram conceptually showing one embodiment of the main body having the identification type instrument assembly in FIG. 6.

The medical apparatus 10A is different from the apparatus 10 in FIG. 4 in that the connection 41 of the instrument assembly IAM (1A–1F) and the tube 22 is a multi connection 41 as shown in FIG. 6.

Correspondingly, the drive switch circuit 71 connects and disconnects the instrument assembly and the drive circuit in the main body 10a. Moreover the identification type instrument assembly IAM (1A–1F) connected to the multi joint connection 41 is specified by the identification means 6, the drive switch circuit 71 selects and switches corresponding drive circuits 7c–7h so as to selectively connect the air circuit 7a and the water circuit 7b.

In this embodiment, because two tubes 22 are introduced from a connection 44 of the main body 10a, the instrument connected to the multi joint connection 41h of each tube 22 is specified and the drive circuit specified for each tube 22 is selected and switched so as to supply air or water.

For example, if the instrument assembly IAM (1A) is connected to the upper multi joint connection 41h (A), the identification means 9 discriminates the identification signals of the identification signal output means 6 housed in the instrument assembly IAM (1A), specifies the instrument assembly IAM (1A) is a turbine handpiece, then control command is sent from the control circuit 7i, the drive switch circuit 71 switches to connect the turbine drive circuit 7c, required air circuit 7a, and air circuit 7b to the multi joint connection 41h (A) so as to supply drive power, air, and water suitable for the instrument IAM (1A).

In the same manner, if the instrument assembly IAM (1C) is connected to the lower multi joint connection 41h (B), the scaler drive circuit 7e, required air circuit 7a, and the water circuit 7b are switched to be connected with the multi joint connection 41h (B) so that drive power, air, and water suitable for the instrument IAM (1C) are supplied.

Accordingly, drive power and so on suitable for the connected instrument assembly can be automatically selected and supplied only by detachably and exchangeably connecting the instrument assembly IAM housing the identification signal output means 6 by means of multi joint connection to the tube 22, and therefore, it is very convenient for an operator.

Figure 8:
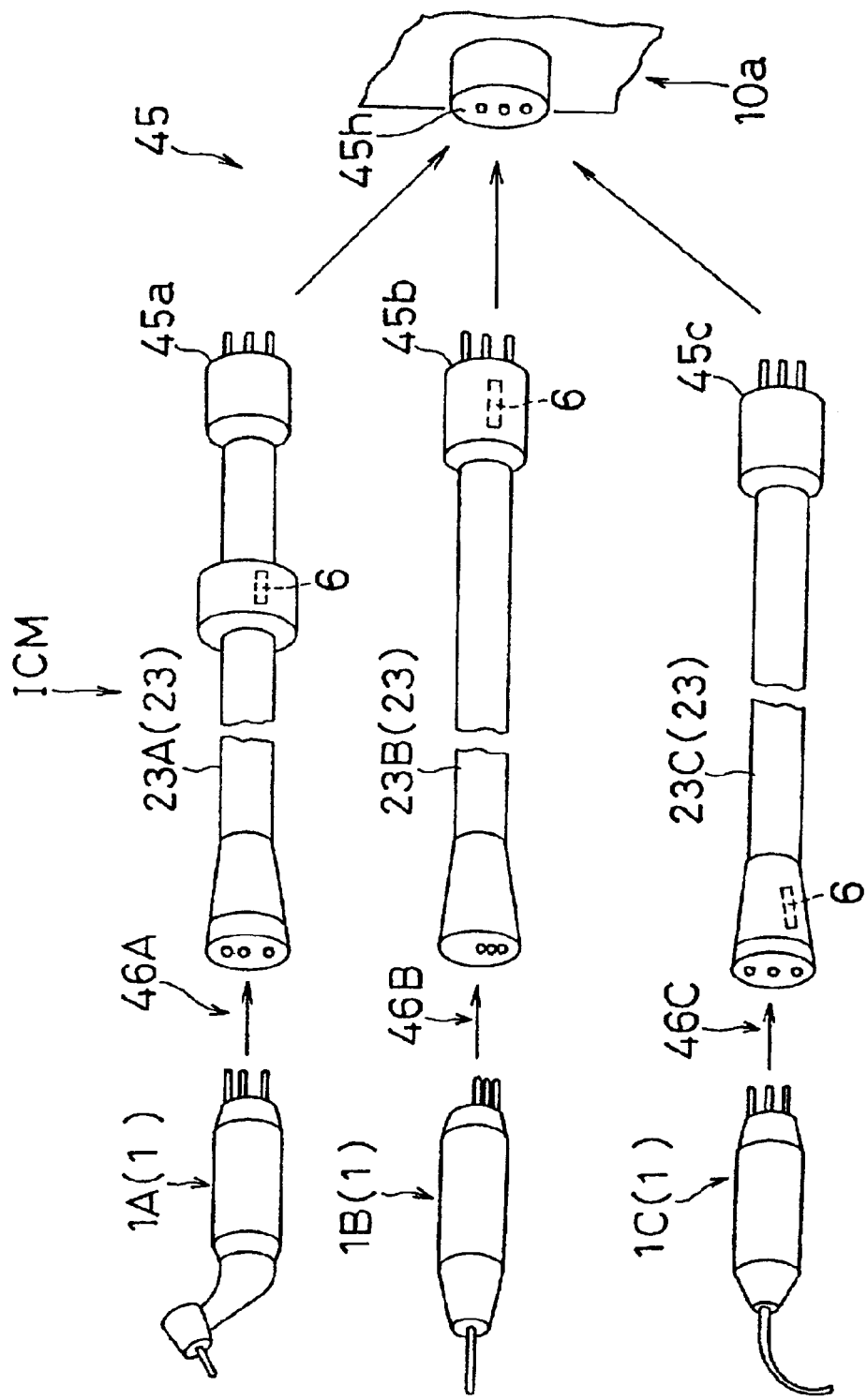
FIG. 8 shows other embodiment of the identification type instrument assembly of the present invention having multi joint connection.

FIG. 8 shows other embodiment of the identification type instrument assembly of the present invention having multi joint connection. The instrument assembly is type ICM in which the instrument and an exclusive tube housing the identification signal output means are combined and connection of the tube and the main body is a multi joint connection.

The identification type instrument assembly ICM (1A, 1B, 1C) is different from FIG. 6 in that the multi joint connection 45 is provided between the main body 10a and a tube 23 comprising the instrument assembly ICM. Tip of tube 23A, 23B, 23C constructs a connection 46A, 46B, 46C respectively corresponding to the instrument 1A, 1B, 1C. The connection 45a, 45b, 45c between the main body 10a is constructed as multi joint connection like the multi joint connection 51 in FIG. 6. The joint 45h provided for the main body 10a is also multi joint connection so that any one of tubes 23A, 23B, 23C can be connected to the main body 10a to be used.

In this case, the identification signal output means 6 is of course housed in the tube 23. It may be housed in the middle of the tube like the tube 23A, in the multi joint connection 45b at main body side like the tube 23B, or in the tip connection 46C side like the tube 23C.

Figure 9:
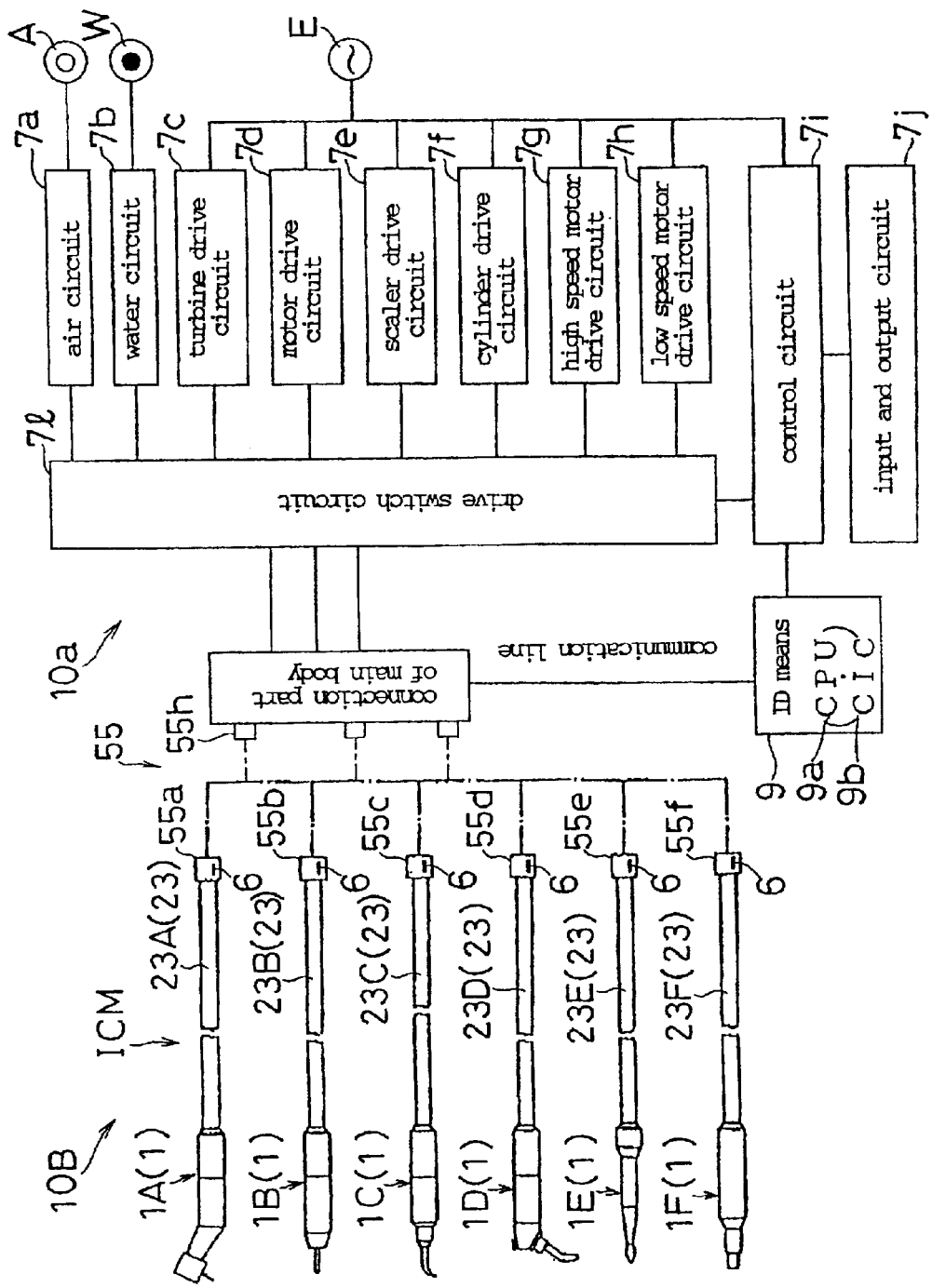
FIG. 9 is a block diagram conceptually showing one embodiment of the medical apparatus having the identification type instrument assembly in FIG. 8.

FIG. 9 is a block diagram conceptually showing one embodiment of the main body having the identification type instrument assembly in FIG. 8.

The main body 10B is different from the main body 10A in FIG. 7 in that the multi joint connection 55 is located between the tube 23 comprising the instrument assembly ICM and the main body 10a, not between the instrument and the tube, but the other construction is the same.

Also under such construction, the instrument assembly ICM connected to three multi joint connections 55h of the main body 10a is specified by the identification signals outputted from the identification signal output means 6 housed in the tube 23, then specified drive circuit is selected and switched per each connection 55h so as to supply air and water.

Figure 10:
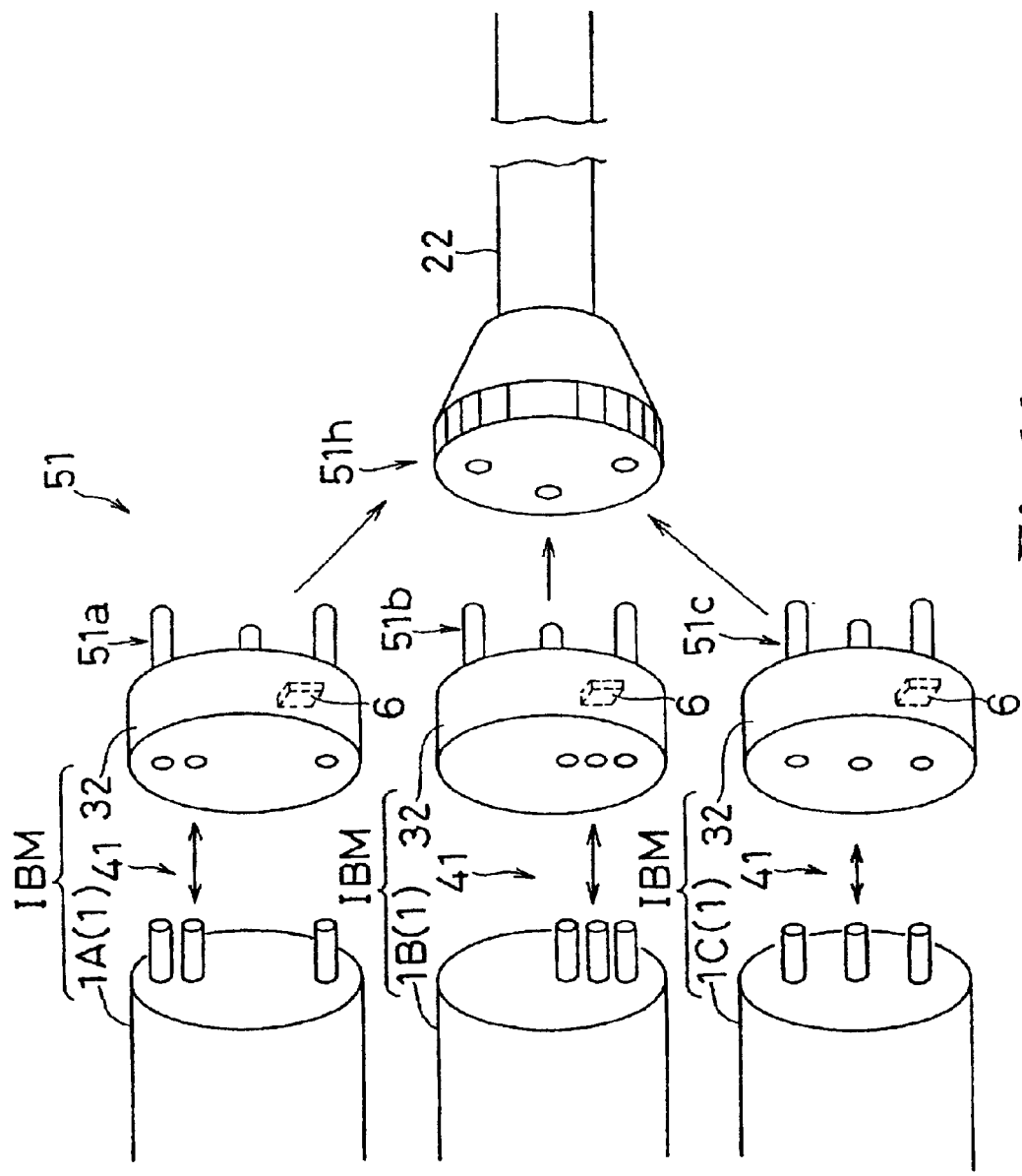
FIG. 10 shows other embodiment of the identification type instrument assembly of the present invention having multi joint connection.

FIG. 10 shows other embodiment of the identification type instrument assembly of the present invention having a multi joint connection. The instrument assembly is type IBM corresponding to a multi joint connection and an exclusive adapter housing the identification signal output means 6 respectively is detachably fitted to the instruments 1A–1C.

The instrument assembly IBM (1A–1C) is the same as the instrument assembly IB in FIG. 5 in that the instrument assembly is combined with the adapter, but is different in that the connection to the tube introduced from the main body is multi joint connection 51.

The connection 41 of the instrument bodies 1A–1C is the same as the instrument assembly IB in FIG. 5, and the connection of the adapter 32 and the tube 22 has the same construction as the connection 51 in FIG. 6.

With such construction, the instrument assembly IBM (1A–1C) is detachably connected to the main body by means of a multi joint connection, the main body specifies the connected instrument by the identification signal output means 6 housed in the adapter 32, then the drive circuit is switched so as to correspond to the specified instrument assembly.

Only the instruments 1A–1C can be autoclaved by separating the instruments 1A–1C from the adapter 32 if the identification signal output means 6 has no resistance to being autoclaved like the instrument IB in FIG. 5.

Figure 11:
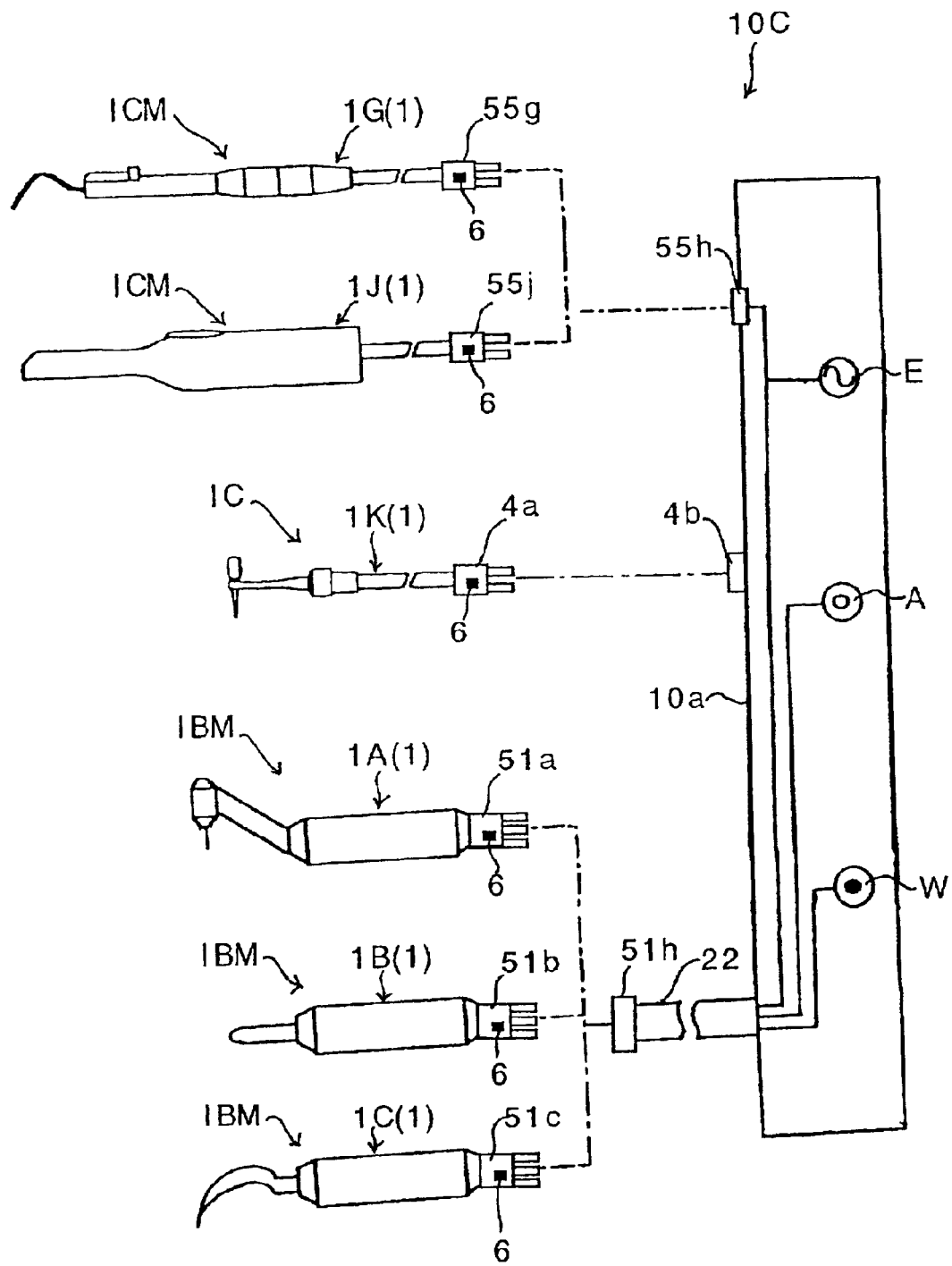
FIG. 11 is a block diagram conceptually showing one embodiment of the medical apparatus having the identification type instrument assembly in FIG. 4, FIG. 8, and FIG. 10.

FIG. 11 is a block diagram conceptually showing one embodiment of the medical apparatus having the identification type instrument bodies in FIG. 4, FIG. 8, and FIG. 10.

According to the medical apparatus 10C, the identification type instrument assembly ICM (1G, 1J) in FIG. 8 in which the end of the tube housing the identification signal output means 6 is multi joint connections 55g, 55j, the identification type instrument assembly IC (1K) in FIG. 4 which is connected to the main body by the connection 4a of the exclusive tube housing the identification signal output means 6, and the instrument assembly IBM (1A, 1B, 1C) in FIG. 10 in which the adapter 32 housing the identification signal output means 6 is detachably fitted and the tube side of the adapter 32 is constructed as a multi joint connection 51a, 51b, 51c are detachably fitted and used.

Correspondingly, the main body 10a has the multi joint connection 55h, a connection 4b exclusive for the instrument IC and the tube 22 having the multi joint connection 51h is introduced.

The instrument assembly ICM (1G) is a photo polymerization means, the instrument ICM (1J) is an intraoral camera, and the instrument assembly IC (1K) is a measuring device of root canal length. The instrument assembly IBM (1A, 1B, 1C) are a turbine handpiece, a motor handpiece, and a scaler respectively.

Under such construction, drive circuits corresponding to the instrument connected by multi joint connection or by an exclusive line are switched to be driven and medical examination can be executed.

Further in such a case, each instrument assembly IBM (1A, 1B, 1C) uses water or air so that the tube is thick. If the thick tube is made multi purpose, the number of the tubes is reduced and a tangle of the tubes hardly happens. Operationality of the tubes isn't deteriorated in case of using exclusive tubes.

On the other hand, because the instrument bodies ICM (1G, 1J) is a photo polymerization means and an intraoral camera, water and air aren't required so that a tube is used for electric source and can be thinner, thereby improving operationality.

Accordingly, the identification type instrument bodies of which multi joint connection is differently located are combined at random and the effects of the multi joint connection can be multi purposely used, the connected instrument assembly can be easily and surely specified, and further the identification means of the main body can be simplified.

If the identification type instrument assembly without a multi joint connection is mixed, the main body can specify the instrument assembly by the same identification means.

Therefore, the above-mentioned several types of the instrument assembly IA, IB, IC, IAM, IBM, ICM may be used by mixture in one medical apparatus.

FIG. 12 shows other embodiment of the main body having the identification type instrument assembly of the present invention, FIG. 12(a) is its entire perspective view, and FIG. 12(b) is a display sample of the display means.

The medical apparatus in FIG. 12(a) uses the instrument assembly IBM in FIG. 10 which is detachably connected to the multi joint connection 51h (not seen in this figure) at the tip end of the tube 22 from the main body 10a (not seen in this figure).

In this figure, display means 8a is comprised of liquid crystal display, input means 8b is comprised of a clear touch panel covering the surface of the liquid crystal display 8a, a dental treatment chair 8c for mounting a patient to examine, a basin table 8d, a side table support arm 8e, a light pole 8f, and a side table 8g are provided. The display means 8a is also used as the input means 8b is provided around the upper part of the side table 8g in such a position that it is easily viewable by an operator working at the side table 8g.

Three tubes 22 are seen and any one of the plural instrument bodies IBM (1) can be detachably and exchangeably fitted. The kind and individuality of the connected instrument assembly IBM (1) are specified by the identification signals output from the identification signal output means and corresponding drive circuit is selected and switched in the main body, so that examination corresponding to the instrument assembly can be executed.

The kind of the instrument assembly IBM (1) connected to the tube 22 is shown on the liquid crystal display means 8a as shown in FIG. 12(b).

This figure shows the individual display of the tube 22 "tube A, tube B, tube C" and shows that the kind of the instrument assembly IBM (1) connected to each tube A, B, C are a motor handpiece, a turbine handpiece, and a scaler.

A window 8aa also has input means 9aa as a touch panel and details of the motor handpiece connected to the tube A are shown in other window 8ab when the button 9aa is drugged to the position of the tube A and clicked. Further, input and confirmation of designated revolution speed can be done using the window as the touch panel 9ab. Namely, display mode and input mode of the specified instrument assembly are automatically prepared and simple selection of the mode can be made, so that it is convenient.

In this case, if there is one the tube 22, it isn't required to select and display mode and input mode corresponding to the kind of the connected instrument is automatically displayed.

The display means 8a and the input means 8b can be used as display means and input means for managing individual record control of the instrument assembly.

Figure 13:
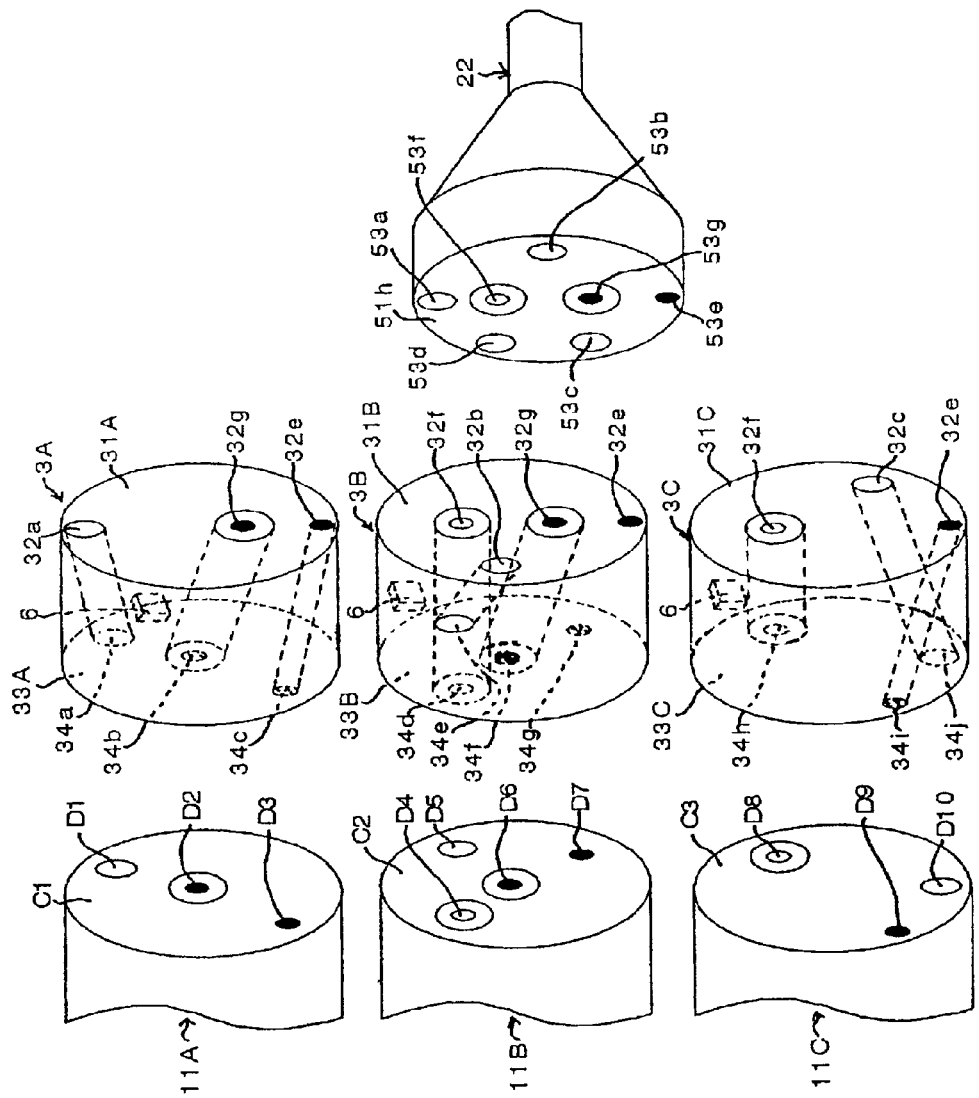
FIG. 13 is a conceptual diagram showing one embodiment of the identification type adapter of the present invention.

FIG. 13 is a conceptual diagram showing one embodiment of the identification type adapter of the present invention.

The identification type adapters 3A, 3B, 3C, detachably connects the instrument 11A, 11B, 11C having connection C1, C2, C3 which isn't multi joint type to the tube 22 having the multi joint connection 51h and have the identification signal output means 6, so that specifying of the instrument 11A, 11B, 11C can be done by the main body 10a.

Connection terminals corresponding to the identification signal output means 6 are provided for each connection, however, they are omitted to be shown so as to prevent complication.

The instrument 11A, 11B, 11C has a connection part C1, C2, C3 and required connection terminals D1–D3, D4–D7, D8–D10 corresponding to its kind. Their positions don't meet the connection terminals 53a–53g of the multi joint connection 51h of the tube 22, therefore, they aren't used for the tube 22 as they are and the adapter 3A, 3B, 3C is used respectively.

The adapter 3A, 3B, 3C has a connection 31A, 31B, 31C at tube side and a connection 33A, 33B, 33C at instrument side respectively. The positions of the terminal connections 32a–32g of the connection 31A, 31B, 31C at tube side are designed to meet the positions of the connection terminals 53a–53g of the tube 22 and its kind corresponds to the requirement of the instrument 11A, 11B, 11C. On the other hand, the connection terminals 34a–34j of the connection 33A, 33B, 33C at the instrument side correspond to the connection terminals D1–D10 of the instrument 11A, 11B, 11C.

Here, the connection terminal 32a, 32g, 32e of the connection 31A at tube side of the adapter 3A is connected to the connection terminal 34a, 34b, 34c of the connection 33A at instrument side respectively, the connection terminal 32b, 32f, 32g, 32e of the connection 31B at tube side of the adapter 3B is connected to the connection terminal 34d, 34e, 34f, 34g of the connection 33B of instrument side, and the connection terminals 32f, 32c, 32e of the connection 31C at tube side of the adapter 3C are connected to the terminal connections 34h, 34i, 34j of the connection 33C of instrument side.

The adapter 3A, 3B, 3C is exclusive for the instrument 11A, 11B, 11C respectively so that the instrument 11A, 11B, 11C can be specified by the identification signals sent from the identification signal output means 6 housed in the adapter 3A, 3B, 3C.

Accordingly when such an adapter 3A, 3B, 3C is used, the instrument 11A, 11B, 11C which doesn't have a multi joint connection can be detachably fitted to the tube 22 having the multi joint connection 51h, the main body can automatically specify the kind of the instrument and switch to the corresponding drive circuit, thereby the instrument can be used.

If the adapter 3A, 3B, 3C is capable of being detached from the instrument 11A, 11B, 11C, only the instrument 11A, 11B, 11C need be autoclaved even if the identification signal output means 6 doesn't have resistance to being autoclaved.

In short, the identification type instrument assembly IBM is constructed by fitting the adapter for the prior instrument which doesn't correspond to a multi joint connection.

Figure 14:
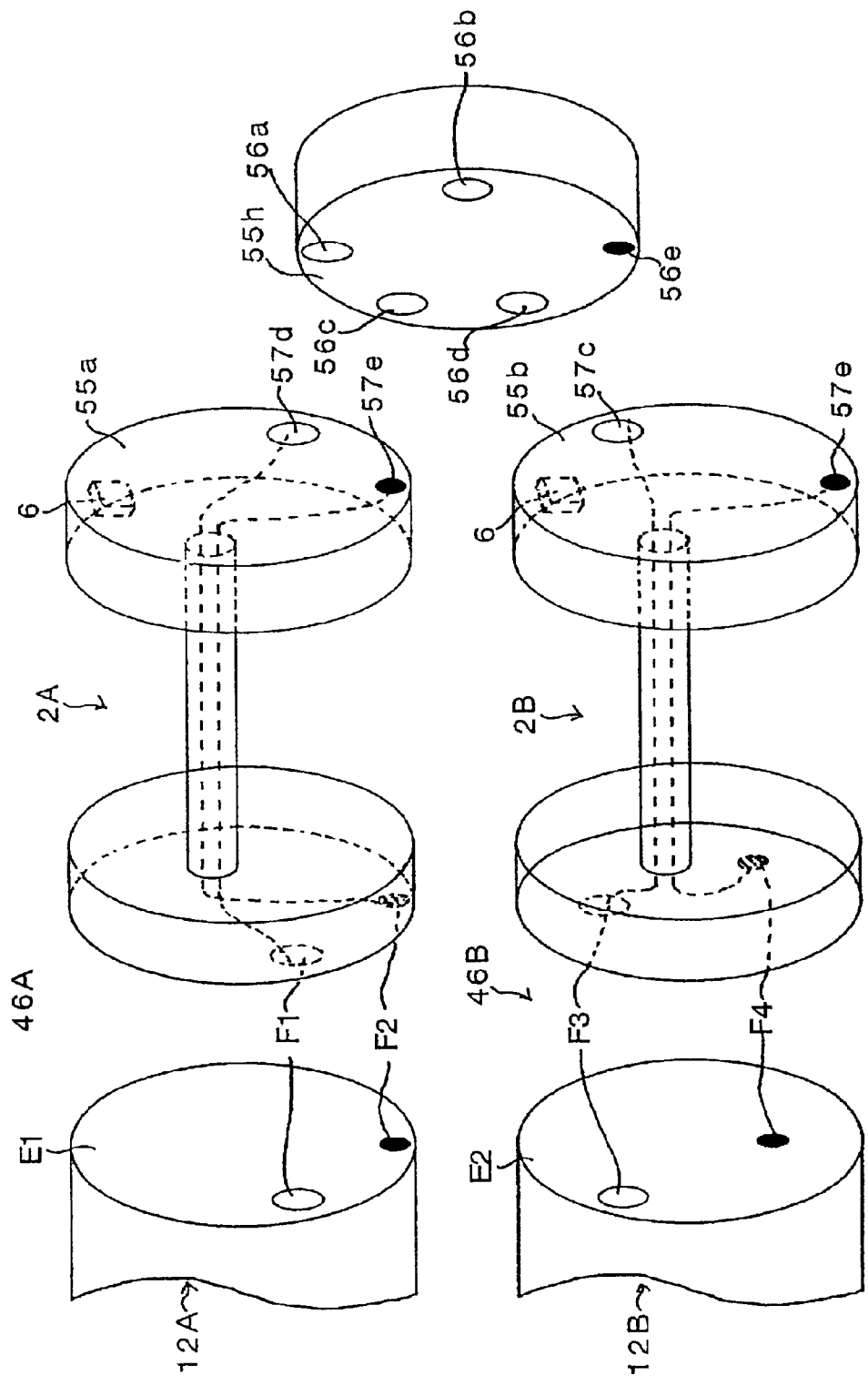
FIG. 14 is a conceptual diagram showing one embodiment of the identification type tube of the present invention.

FIG. 14 is a conceptual diagram showing one embodiment of the identification type tube of the present invention.

The idea of the identification type adapter in FIG. 13 is diverted to an identification type tube 2A, 2B. If the tube 2A, 2B is used, the instrument 12A, 12B which isn't a multi joint type can be detachably connected to the multi joint connection 55h provided for the main body and the tube 2A, 2B includes the identification signal output means 6, so that kind of the instrument can be specified.

A connection 46A, 46B is exclusively connected to the instrument 12A, 12B by connection terminals F1, F2, F3, F4 exclusive for the instrument 12A, 12B respectively. On the other hand, a connection 55a, 55b of the tube 2A, 2B is multi joint type, connection terminals 57d, 57e, 57c, 57e corresponding to the connection terminals F1, F2, F3, F4 of the instrument 12A, 12B are provided at the same position of the connection terminals 56a–56e of the multi joint connection 55h of the main body, and the connection terminal 46A, 46B at instrument side and 55a, 55b at main body side are corresponded and connected like the adapter in FIG. 11.

Therefore, when the instrument 12A, 12B is connected to the main body through such a tube 2A, 2B, the same effect as with the adapter can be achieved. In other words, the identification type instrument assembly ICM can be constructed by fitting such an identification type tube to the conventional instrument which isn't multi joint type.

Figure 15:
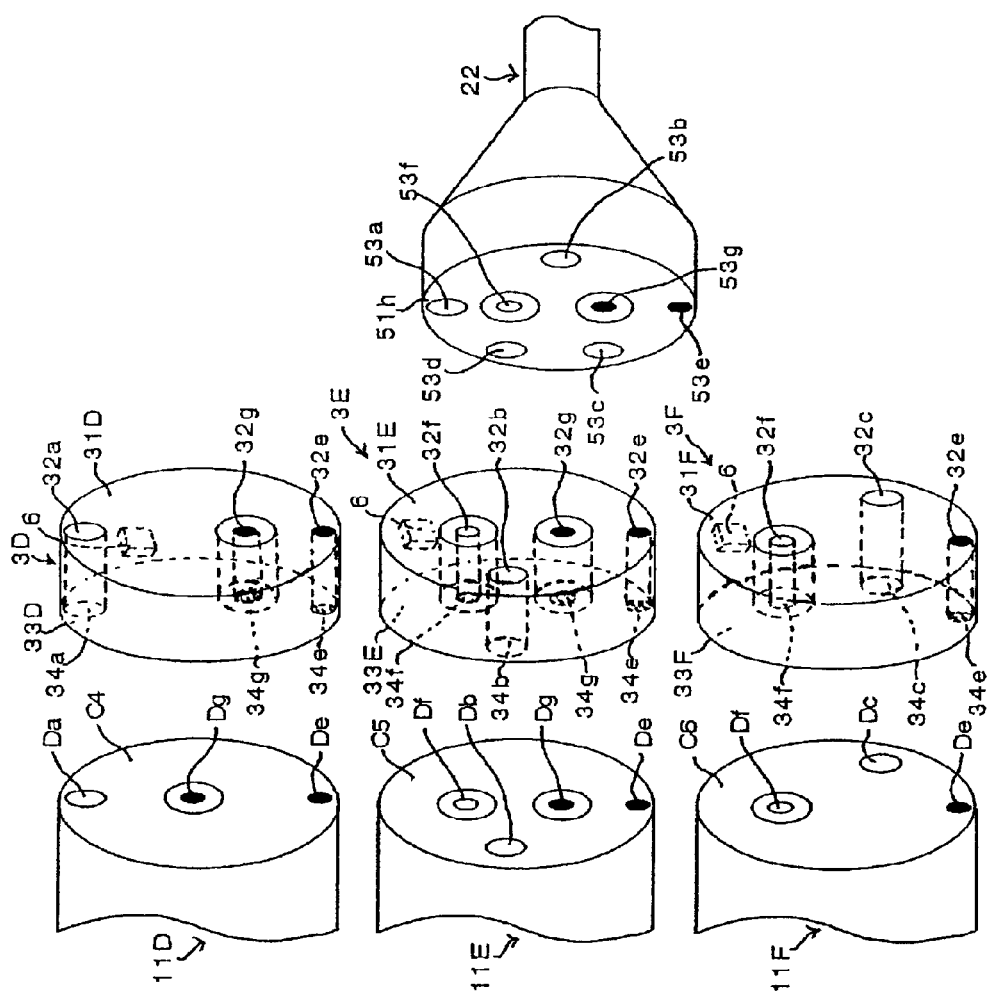
FIG. 15 is a conceptual diagram showing other embodiment of the identification type adapter of the present invention.

FIG. 15 is a conceptual diagram showing other embodiment of the identification type adapter of the present invention.

An identification type adapter 3D, 3E, 3F is used when an instrument 11D, 11E, 11F is of a multi joint type but doesn't includes the identification signal output means.

A connection 31D, 31E, 31F of the adapter 3D, 3E, 3F at tube side is the same as the connection 31A, 31B, 31C of the adapter 3A, 3B, 3C at tube side and the same kinds of the connection terminals 34a–34g of the connection 33D, 33E, 33F at instrument side as those of tube side are provided at the same position. Connection terminals Da–Dg of the instrument 11D, 11E, 11F are the same and any connections are multi joint type.

In this case, the adapter 3D, 3E, 3F is exclusive for the instrument 11D, 11E, 11F, so that the instrument 11D, 11E, 11F can be specified by the identification signals output from the identification signal output means 6 housed in the adapter 3D, 3E, 3F.

Thus the instrument which is a multi joint type but doesn't correspond to identification signal output type can be made to be an identification signal output corresponding type by inserting the adapter 3D, 3E, 3F. Further, when the adapter 3D, 3E, 3F is capable of detachably connecting to the instrument 11D, 11E, 11F respectively, only the instrument 11D, 11E, 11F need be autoclaved and it has no trouble if the identification signal output means 6 doesn't have resistance to being autoclaved.

Namely, an identification type instrument assembly IBM can be constructed by fitting the identification type adapter to the conventional multi joint type instrument which doesn't actively transmit identification signals.

Further, the adapter 3D, 3E, 3F may be commonly used and connection terminals which are the same kind and position as those for the multi joint connection 51h of the main body may be provided. In such a case, the adapter isn't exclusive for the instrument, but it may be provided with higher process function by the housed identification signal output means, measure the resistance and impedance of the connected instrument, and specify the kind of the instrument by the measured result, so that data of the kind may be output to the main body.

Figure 16:
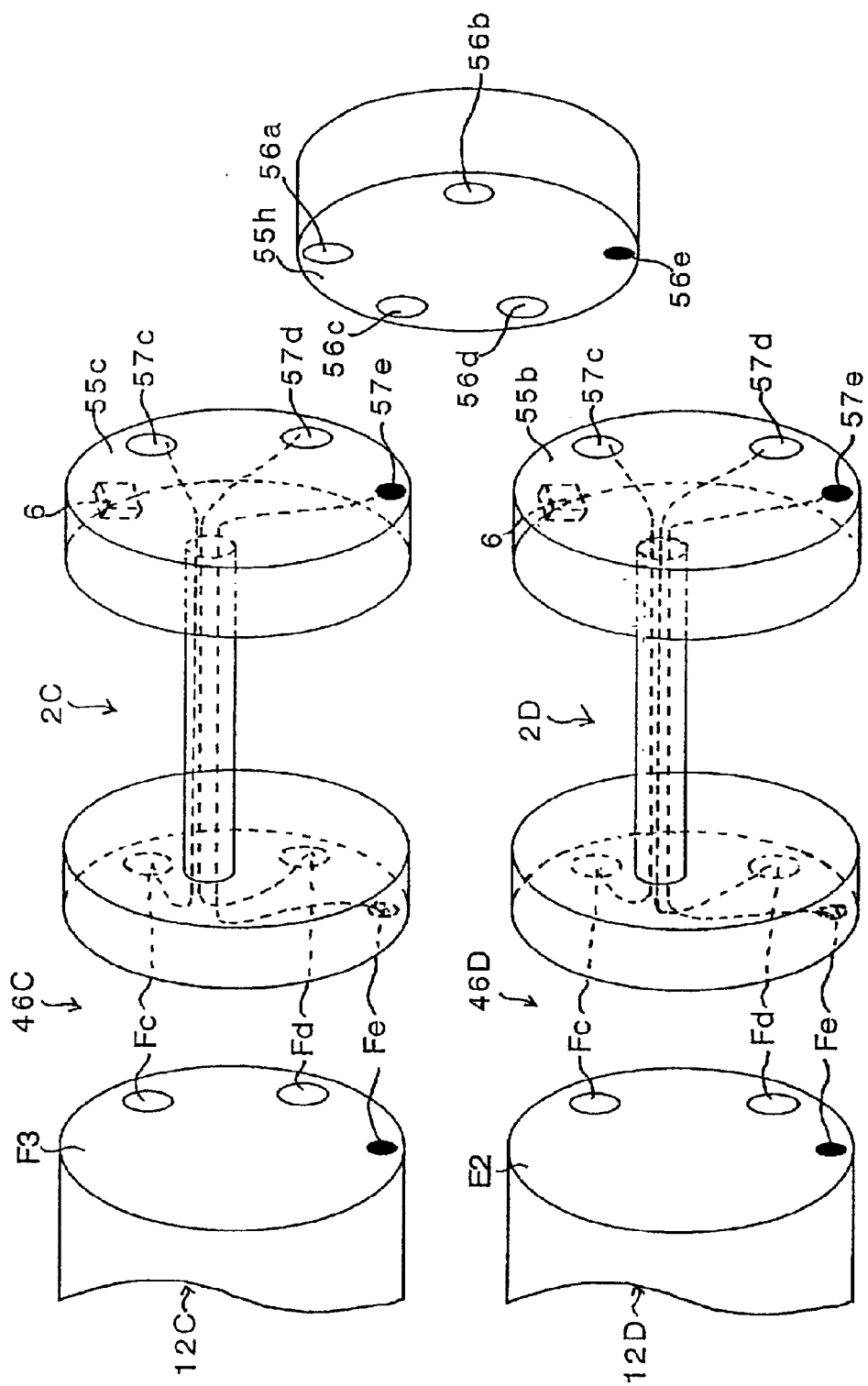
FIG. 16 is a conceptual diagram showing other embodiment of the identification type tube of the present invention.
Figure 17:
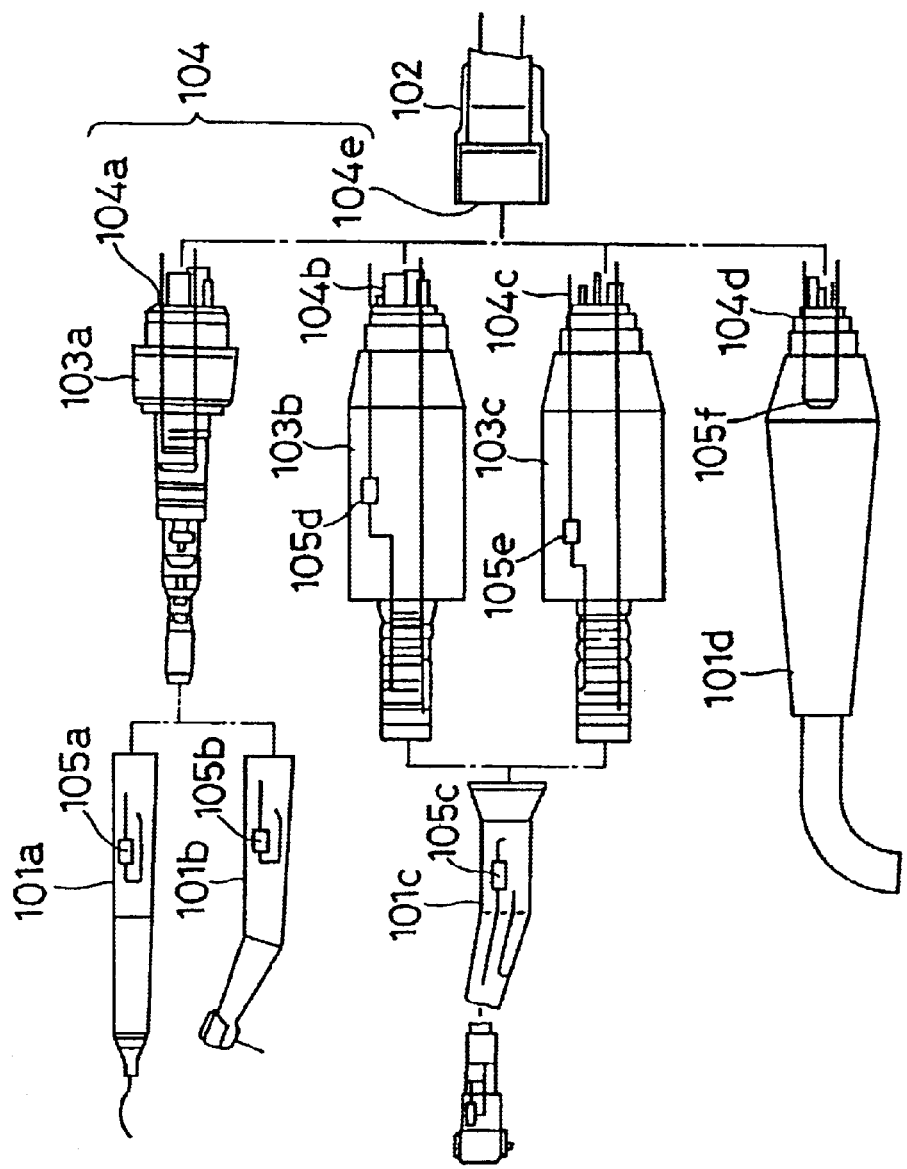
FIG. 17 shows one embodiment of the conventional instrument assembly.
Figure 18:
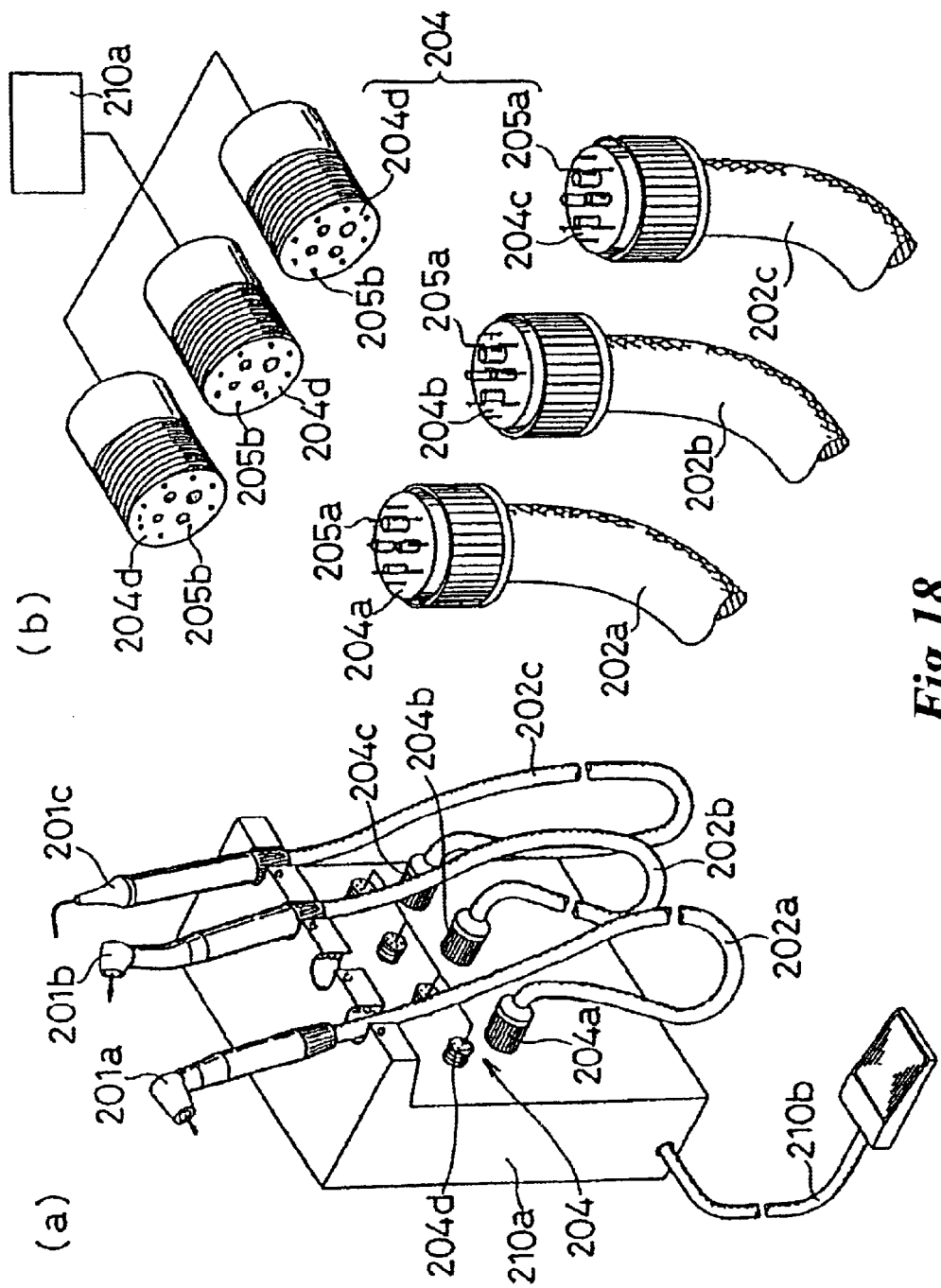
FIG. 18 shows other embodiment of the conventional instrument assembly, FIG. 18($a$) is an outline view showing its usage, and FIG. 18($b$) shows details of its connection.
Figure 19:
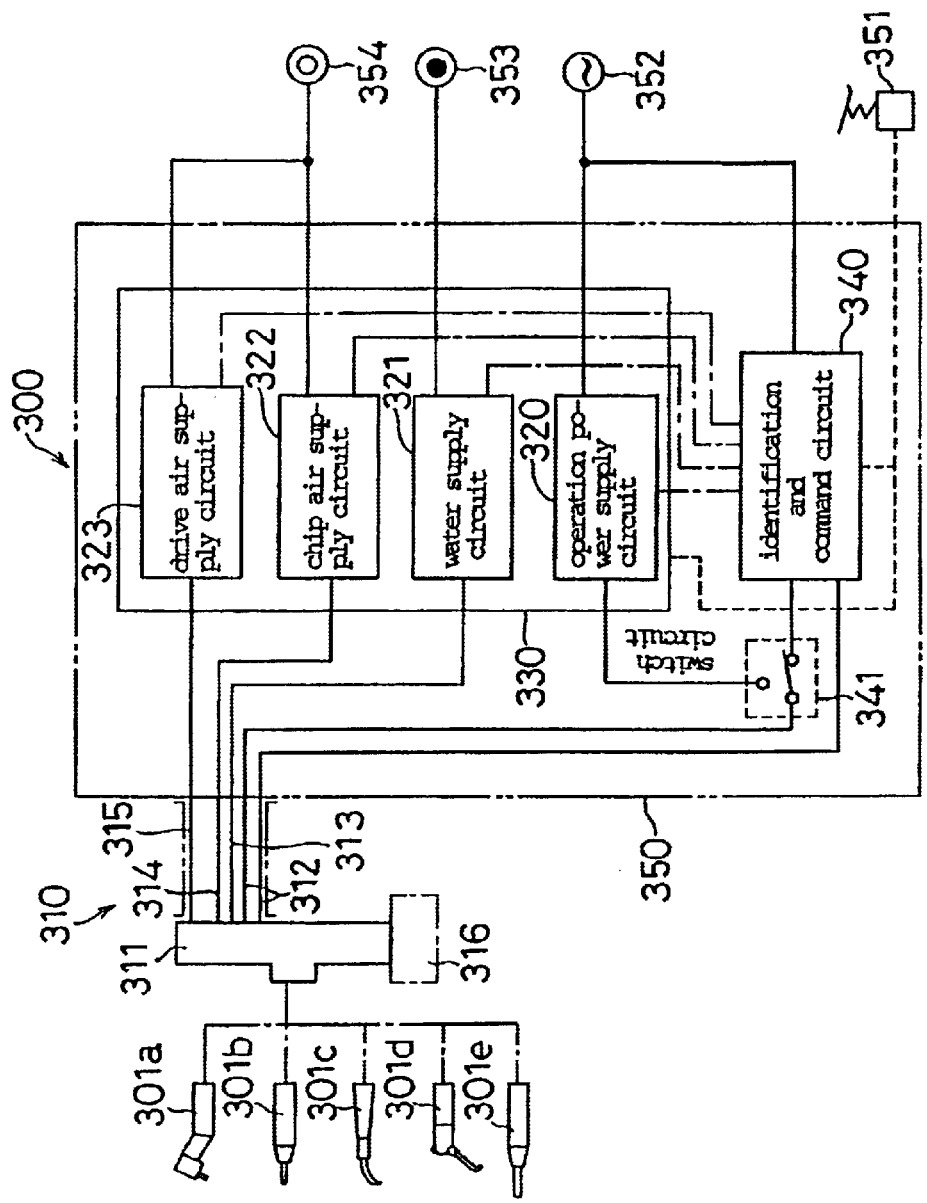
FIG. 19 is a block diagram showing one embodiment of the medical apparatus having the conventional instrument assembly.
Figure 20:
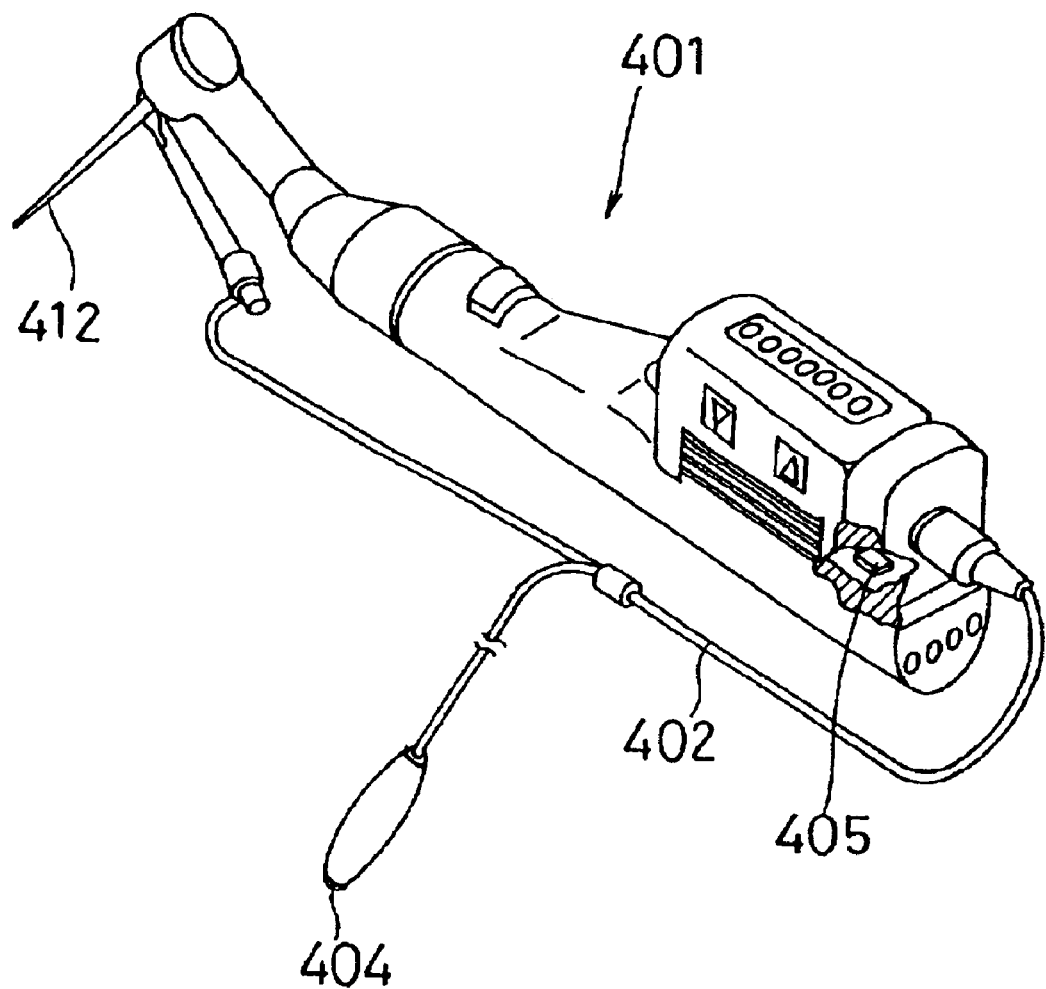
FIG. 20 shows an embodiment of the instrument assembly.

FIG. 16 is a conceptual diagram showing other embodiment of the identification type tube of the present invention.

The idea of the identification type adapter in FIG. 15 is diverted to the identification type tube 2C, 2D. If the tube 2C, 2D is used, the instrument 12C, 12D which is multi joint type but doesn't correspond to identification signal output can be detachably connected to the multi joint connection 55h provided for the main body so that kind of the instrument 12C, 12D can be specified by the identification signal output means 6.

Connection 46C, 46D of the tube 2C, 2D at instrument side is connected to the instrument 12C, 12D by a connection terminal Fc, Fd, Fe respectively. On the other hand, a connection 55c, 55d of the tube 2C, 2D at main body side of the tube 2C, 2D is multi joint type, a connection terminal 57c, 57d, 57e, corresponding to the connection terminal Fc, Fd, Fe of the instrument 12C, 12D are provided at the same position of the connection terminals 56a–56e of the multi joint connection 55h of the main body, and the connection terminals at instrument side and at main body side correspond and are connected like the adapter in FIG. 15.

Therefore, when the instrument 12C, 12D is connected to the main body through such a tube 2C, 2D, the same effect as the adapter can be achieved.

In other words, the identification type instrument assembly ICM can be constructed by fitting such an identification type tube to the conventional multi joint type instrument which doesn't actively transmit identification signals.

What is claimed is:

1. An identification type instrument assembly detachably connected to a main body of a medical apparatus for use in diagnosis and treatment;
   wherein said instrument assembly comprises an identification signal output means for actively outputting ID code being serial data, said ID code being self-identification signals prepared in advance for identifying said instrument assembly,
   wherein said identification signal output means sends said self-identification signals to said main body when receiving electric power from said main body upon connecting said identification type instrument assembly to said main body; and
   wherein said instrument assembly is automatically connected to a drive circuit or a control circuit which is provided in said main body corresponding to the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

2. An identification type instrument assembly detachably connected to a main body of a medical apparatus for use in diagnosis and treatment, comprising:
   an instrument and,
   an adapter detachably fitted to said instrument for connecting said instrument to said main body, said adapter housing an identification signal output means for actively outputting ID code being serial data, said ID code being self-identification signals prepared in advance,
   wherein said identification signal output means sends said self-identification signals to said main body when receiving electric power from said main body upon connecting said identification type instrument assembly to said main body via said adapter; and
   wherein said instrument assembly is automatically connected to a drive circuit or a control circuit which is provided in said main body corresponding to the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

3. An identification type instrument assembly detachably connected to a main body of a medical apparatus for use in diagnosis and treatment, comprising;
   an instrument and,
   a tube detachably fitted to said instrument for connecting said instrument to said main body, said tube housing identification signals outputs means for actively outputting ID code being serial data said ID code being self-identification signals prepared in advance,
   wherein said identification signal output means sends said self-identification signals to said main body when receiving electric power from said main body upon connecting said identification type instrument assembly to said main body via said tube, and
   wherein said instrument assembly is automatically connected to a drive circuit or a control circuit which is provided in said main body corresponding to the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

4. The identification type instrument assembly as set forth in any one of claims 1–3, wherein said identification signal output means is comprised as a microcomputer element or a communication integration element.

5. The identification type instrument assembly as set forth in any one of claims 1–3, wherein said identification signal output means is provided with nonvolatile storage means and serial data, voltage level signals of which wave height value is varied at a predetermined repetition cycle, or frequency identification signals of which frequency is varied is outputted as said identification signal from said identification signal output means, based on the data stored in said nonvolatile storage means.

6. The identification type instrument assembly as set forth in any one of claims 1–3, wherein a connection part for detachably connecting said instrument assembly to said main body is a multi junction connection.

7. The identification type instrument assembly as set forth in claim 1, wherein said instrument assembly is comprised of an instrument and an adapter detachably fitted to the instrument and is capable of detachably connecting to a tube introduced from said main body via said adapter, said identification signal output means is provided for said adapter, and connection between said adapter and said tube is multi junction connection.

8. The identification type instrument assembly as set forth in claim 1, wherein said instrument assembly is comprised of an instrument and a tube detachably fitted to the instrument and is capable of detachably connecting to said main body via said tube, said identification signal output means is provided for said tube, and connection between said tube and said main body is multi junction connection.

9. An identification type adapter detachably attached to an instrument assembly, detachably connected to a main body of a medical apparatus for use in diagnosis and treatment, wherein said adapter comprises an identification signal output means for actively outputting ID code being serial data, said ID code being self-identification signals prepared in advance for identifying attached instrument assembly, wherein said identification signal output means sends said self-identification signals to said main body when receiving electric power from said main body upon connecting said adapter to said main body, and wherein said instrument assembly is automatically connected to a drive circuit or a control circuit which is provided in said main body corresponding to the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

10. The identification type adapter as set forth in claim 9, wherein a connection part for detachably connection said adapter to said main body is multi junction connection.

11. An identification type tube detachably attached to an instrument assembly detachably connected to a main body of a medical apparatus for use in diagnosis and treatment, wherein said tube comprises identification signal output means for actively outputting ID code being serial data, said ID code being self-identification signals prepared in advance for identifying attached instrument assembly, wherein said identification signal output means sends said self-identification signals to said main body when receiving electric power from said main body upon connection said tube to said main body, and wherein said instrument assembly is automatically connected to a drive circuit or a control circuit which is provided in said main body corresponding to the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

12. The identification type tube as set forth in claim 11, wherein a connection part for detachably connecting said tube to said main body is a multi junction connection.

13. A medical apparatus for use in diagnosis and treatment with a main body to which an instrument assembly is detachably connected, wherein said instrument assembly is comprised as an instrument assembly having an identification signal output means for actively outputting ID code being serial data, said ID code being self-identification signals prepared in advance for identifying attached instrument assembly, wherein said identification signal output means sends said self-identification signals to said main body when receiving electric power from said main body upon being connected to said main body, and wherein said instrument assembly is automatically connected to a drive circuit or a control circuit which is provided in said main body corresponding th the type of said instrument assembly, a water supply circuit, an air supply circuit, or a power supply circuit corresponding to the type of plural kinds of instrument assemblies is selectively driven when said main body decodes said identification signal from said instrument assembly and identifies said instrument assembly.

14. The medical apparatus as set forth in claim 13, wherein when said instrument assembly is specified, display mode of display means and/or input mode of input means such as a touch panel can be automatically switched corresponding to the specified instrument assembly.

15. The medical apparatus as set forth in claim 13 or 14, wherein when said instrument assembly is specified, management of usage history and distinction of using operator of the specified instrument assembly can be executed.

16. The medical apparatus as set forth in claim 13 or 14, wherein said main body is provided with a microcomputer element or an integrated element for communication as identification means of identification signals output from said identification signal output means of the connected instrument assembly.

17. The medical apparatus as set forth in claim 13 or 14, wherein wiring to a connection part detachably connecting said instrument assembly in said main body is a multi-branch structure.

* * * * *